(12) United States Patent
Mitchell et al.

(10) Patent No.: US 11,887,060 B1
(45) Date of Patent: *Jan. 30, 2024

(54) INTELLIGENT FILE-LEVEL VALIDATION

(71) Applicant: CollectiveHealth, Inc., San Francisco, CA (US)

(72) Inventors: Alden Mitchell, San Francisco, CA (US); Kristianne Martinez-Fonts, San Francisco, CA (US); Bhargavi Damodaran, Sunnyvale, CA (US); Andrew Siu, San Francisco, CA (US); Evan Leichter, San Francisco, CA (US); Mayuri Karra, Foster City, CA (US)

(73) Assignee: CollectiveHealth, Inc., San Mateo, CA (US)

( * ) Notice: Subject to any disclaimer, the term of this patent is extended or adjusted under 35 U.S.C. 154(b) by 526 days.

This patent is subject to a terminal disclaimer.

(21) Appl. No.: 17/099,265

(22) Filed: Nov. 16, 2020

Related U.S. Application Data

(63) Continuation of application No. 15/889,034, filed on Feb. 5, 2018, now Pat. No. 10,839,352.

(51) Int. Cl.
| | |
|---|---|
| *G06Q 10/1057* | (2023.01) |
| *G16H 10/60* | (2018.01) |
| *G06F 16/23* | (2019.01) |
| *G06F 16/27* | (2019.01) |
| *G06N 20/00* | (2019.01) |

(52) U.S. Cl.
CPC ..... *G06Q 10/1057* (2013.01); *G06F 16/2365* (2019.01); *G06F 16/27* (2019.01); *G06N 20/00* (2019.01); *G16H 10/60* (2018.01)

(58) Field of Classification Search
None
See application file for complete search history.

(56) References Cited

U.S. PATENT DOCUMENTS

| | | |
|---|---|---|
| 2003/0191667 A1 | 10/2003 | Fitzgerald et al. |
| 2013/0204757 A1 | 8/2013 | Willard et al. |
| 2014/0081652 A1 | 3/2014 | Klindworth |

(Continued)

OTHER PUBLICATIONS

Non Final Office Action dated Jan. 9, 2020 for U.S. Appl. No. 15/889,034 "Intelligent File-level Validation" Mitchell, 22 pages.

(Continued)

*Primary Examiner* — Dennis W Ruhl
(74) *Attorney, Agent, or Firm* — Lee & Hayes, P.C.

(57) ABSTRACT

Intelligent file-level validation is described. A service provider (e.g., an administrator) can determine rule(s) based partly on specified data. The service provider can receive a data file. The service provider can determine modification data that indicates an amount of change to result from modifying previously stored data based on the data file, and can analyze the modification data based partly on threshold(s) associated with the rule(s). Each threshold can indicate an amount of change that is determined to be permissible for the data file, for the corresponding rule. The service provider can determine whether the data file is valid based partly on analyzing the modification data in view of the rule(s). Valid data files can be stored in a database that represents a source of truth and invalid data files can be routed to error handling.

20 Claims, 6 Drawing Sheets

(56) References Cited

U.S. PATENT DOCUMENTS

2016/0048758 A1   2/2016   Campbell

OTHER PUBLICATIONS

Final Office Action dated Apr. 3, 2020 for U.S. Appl. No. 15/889,034 "Intelligent File-level Validation", Mitchell, 18 pages.
Ward, et. al., "Effects of Common Data Errors in Electronic Health Records on Emergency Department Operational Performance Metrics: A Monte Carlo Simulation" Acad Emerg Med, vol. 22, Iss. 9, Sep. 2015, pp. 1085-1092.

500 ⟶

```
┌─────────────────────────────────────────────────────────────────────┐
│   DETERMINE, FOR A DATA FILE ASSOCIATED WITH A SPONSOR, AT LEAST    │
│   ONE OF ATTRIBUTE(S) ASSOCIATED WITH THE SPONSOR, ATTRIBUTE(S)     │
│   ASSOCIATED WITH A SPONSOR SERVICE PROVIDER, ATTRIBUTE(S)          │
│   ASSOCIATED WITH A PARTNER, ATTRIBUTE(S) ASSOCIATED WITH A         │
│   RECORD OR A SET OF RECORDS, A TIME OF DAY, A TIME OF MONTH,       │
│   A TIME OF YEAR, OR A SEASON                                       │
│                              502                                    │
└─────────────────────────────────────────────────────────────────────┘
                                 │
                                 ▼
┌─────────────────────────────────────────────────────────────────────┐
│  DETERMINE, BASED AT LEAST IN PART ON A DATA MODEL AND AT LEAST     │
│  ONE OF ATTRIBUTE(S) ASSOCIATED WITH THE SPONSOR, ATTRIBUTE(S)      │
│  ASSOCIATED WITH THE SPONSOR SERVICE PROVIDER, ATTRIBUTE(S)         │
│  ASSOCIATED WITH THE PARTNER, ATTRIBUTE(S) ASSOCIATED WITH THE      │
│  RECORD OR THE SET OF RECORD(S), THE TIME OF DAY, THE TIME OF       │
│  MONTH, THE TIME OF YEAR, OR THE SEASON, A THRESHOLD                │
│  ASSOCIATED WITH A RULE, THE THRESHOLD INDICATING AN AMOUNT         │
│  OF CHANGE THAT IS PERMISSIBLE FOR THE SPONSOR AND/OR THE DATA FILE │
│                              504                                    │
└─────────────────────────────────────────────────────────────────────┘
                                 │
                                 ▼
┌─────────────────────────────────────────────────────────────────────┐
│  COMPARE THE THRESHOLD WITH MODIFICATION DATA ASSOCIATED WITH       │
│  THE DATA FILE TO DETERMINE WHETHER THE DATA FILE IS VALID          │
│                              506                                    │
└─────────────────────────────────────────────────────────────────────┘
```

FIG. 5

INTELLIGENT FILE-LEVEL VALIDATION

PRIORITY

This application is a continuation of, and claims priority to, pending U.S. patent application Ser. No. 15/889,034, filed on Feb. 5, 2018, entitled "INTELLIGENT FILE-LEVEL VALIDATION", now known as U.S. Pat. No. 10,839,352, issued on Nov. 17, 2020, which is fully incorporated by reference herein.

BACKGROUND

Administrators process claims and/or certain other aspects of employee benefit plans on behalf of themselves and/or other entities, such as employers. To process claims and/or certain aspects of employee benefit plans, administrators often determine which subscribers (e.g., employees that elect to participate in employee benefit plans) are eligible for particular benefits. To do so, administrators can process significant amounts of data related to eligibility and must make complex, often fact-specific determinations that often involve analyzing data from multiple sources, in multiple formats, from multiple jurisdictions, at multiple times, pertaining to multiple individuals, benefit plans, and entities, which can be subject to multiple laws, rules, and regulations.

As described above, administrators can receive data from multiple data sources (e.g., employers, providers, vendors, etc.), which can be sent across multiple systems. Each of the data sources submits such data on its own timelines, standards, formats, etc. Additionally, such data can change frequently and can include errors. Furthermore, the transmission of such data can introduce errors. Inaccurate data can cause significant disruptions. For instance, eligibility issues can cause patient disruption when accessing care (which can impair or prevent patients from accessing care in times of need) and/or data loss (which can impair the integrity and availability of information for building health and/or other benefit plans).

Currently, efficiency and accuracy in error resolution are driven through complex operational procedures, manual reviews, and spreadsheets. Such efforts rely heavily upon reviewing and flagging errors in individual (subscriber-level) records, sending suspect or erroneous data back to the source of the data for correction, and waiting until the data source sends corrections and/or updated data. Recurring errors may persist, causing multiple cycles of review and correction as described above. Accordingly, claim and plan administration can be time-consuming, laborious, error-prone, and costly. Administrators invest significant computational, human, and financial resources to ensure data accuracy to streamline insurance claim and/or employee benefit plan processing.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 5 illustrates an example process for determining a threshold for validating a data file.

DETAILED DESCRIPTION

Figure 1:
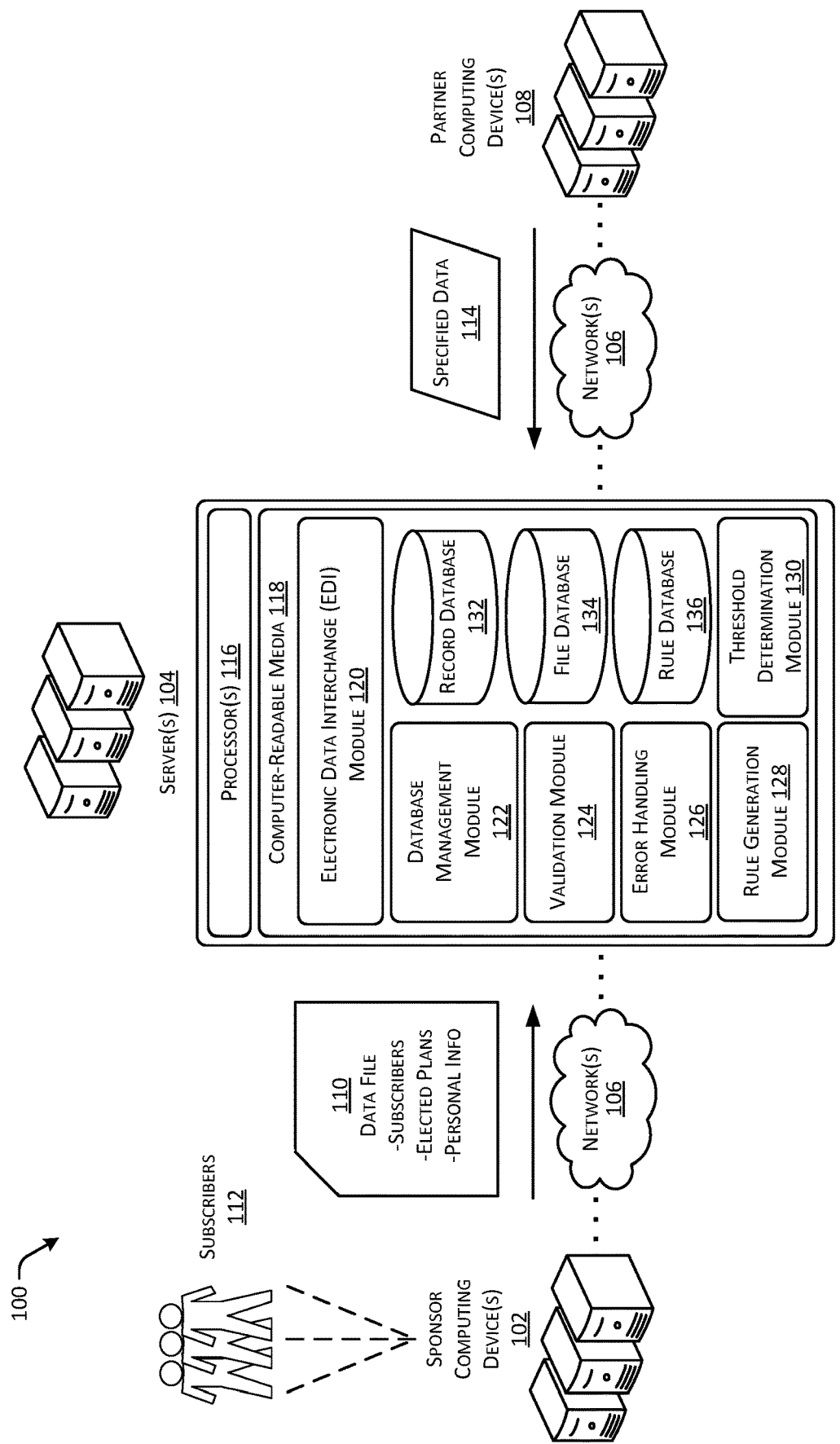
FIG. 1 illustrates a system for facilitating intelligent file-level validation.

This disclosure describes intelligent file-level validation. As described herein, administrators process claims and/or certain other aspects of employee benefit plans on behalf of themselves and/or other entities, such as employers. To process claims and/or certain aspects of employee benefit plans, administrators often determine which subscribers are eligible for particular benefits. To do so, administrators process significant amounts of data associated with eligibility and must make complex, often fact-specific determinations that often involve analyzing data from multiple sources, in multiple formats, from multiple jurisdictions, at multiple times, pertaining to multiple individuals, benefit plans, and entities, which can be subject to multiple laws, rules, and regulations.

Such data is received from multiple data sources (e.g., employers, providers, vendors, etc.), which can be sent across multiple systems. For the purpose of this discussion, employers can be referred to as "sponsors." In at least one example, sponsors can provide healthcare and/or other employee benefit plans to employees, who can be referred to as "subscribers." That is, a subscriber can be an employee that elects to participate in and/or is otherwise defaulted in to a healthcare and/or other employee benefit plan. An employee can have one or more dependents that can be associated with the same subscriber. Providers, vendors, etc. can be referred to as "partners" for the purpose of this discussion. Partners can specify the scope of healthcare and/or other employee benefit plans (e.g., specify the benefit(s)) and set eligibility requirements for receiving such benefits. By way of example and not limitation, partners can include insurance providers and/or vendors, incentive providers and/or vendors, wellness providers and/or vendors, etc. In some examples, a partner can be an internal entity (e.g., team, working group, department, etc.) associated with an administrator.

In at least one example, subscribers, sponsors, partners, and/or other entities (e.g., healthcare providers (e.g., hospitals, doctors, etc.), etc.) can send data to an administrator for processing claims and/or other aspects of employee benefit plans. As described above, each of the subscribers, sponsors, partners, and/or other sources (e.g., healthcare providers, etc.) can submit such data on its own timeline, standard, format, etc. Additionally, such data can change frequently and can include errors. Furthermore, the transmission of such data can introduce errors. Inaccurate data can cause significant disruptions. For instance, eligibility issues can cause patient disruption when accessing care (which can impair or prevent patients from accessing care in times of need) and/or data loss (which can impair the integrity and availability of information for building health and/or other benefit plans).

As mentioned above, efficiency and accuracy in error resolution are driven through complex operational procedures, manual reviews, and spreadsheets. Such efforts rely heavily upon reviewing and flagging errors in individual (subscriber-level) records, sending suspect or erroneous data back to the source of the data for correction, and waiting until the data source sends corrections and/or updated data. Recurring errors may persist, causing multiple cycles of review and correction as described above. Accordingly, claim and plan administration can be time-consuming, laborious, error-prone, and costly. As a result, administrators often invest significant resources—computational, human, and financial—into ensuring data accuracy to streamline claim and/or employee benefit plan processing.

Accurate data is a concern for administrators as well as subscribers, sponsors, partners, and/or other entities (e.g., healthcare providers, etc.) because each entity requires accurate data for individual usage. Accordingly, computing systems handling operations for administrators, subscribers, sponsors, partners, and/or other entities (e.g., healthcare providers, etc.) often allocate a significant amount of computational resources to processing incoming data and analyzing such data for errors. Similarly, due to the number of errors identified in such data, administrators, subscribers, sponsors, partners, and/or other entities (e.g., healthcare providers, etc.) often require a significant amount of computational resources for transmitting erroneous data files between respective computing systems for correction and re-transmission. That is, provisioning data associated with eligibility and ensuring that such data is accurate is computationally expensive.

Techniques described herein are directed to systematically identifying, correcting, and learning (e.g., via machine-learning mechanisms) expected aggregate data file behavior to streamline data error detection and handling. In at least one example, techniques described herein enable intelligent file-level validation by computing system(s) associated with an administrator. That is, techniques described herein describe receiving a new data file, analyzing the new data file to identify changes to be implemented by the new data file (e.g., determine to what extent a database storing eligibility data associated with subscriber(s) will change based on the new data file, determine change between the new data file and a previously validated data file, etc.), and based on identifying the changes to be implemented, determining whether the new data file is valid. Responsive to determining that a new data file is valid, techniques described herein can add the new data file to database(s) associated with the computing system(s) to update eligibility data associated with subscribers. As used herein, a "new data file" can represent a data file that is completely new to the recipient and/or a data file that includes at least some data that has been previously submitted and some new data (e.g., a modified data file).

In at least one example, the database(s) can store data that serves as the source of truth of eligibility data for subscribers, sponsors, partners, and/or other entities (e.g., healthcare providers, etc.). That is, the database(s) can store eligibility data in a centralized location such that subscribers, sponsors, partners, and/or other entities (e.g., healthcare providers, etc.) have a single access point for eligibility data, and that each of the subscribers, sponsors, partners, and/or other entities (e.g., healthcare providers, etc.) are making decisions based on and/or otherwise using the same eligibility data. Accordingly, techniques described herein are directed to providing an integrated snapshot of (validated) subscriber eligibility across subscribers, sponsors, partners, and/or other entities (e.g., healthcare providers, etc.) for downstream use.

Techniques described herein can utilize rules and thresholds to validate incoming data files. The rules and/or thresholds can be predetermined or dynamically determined and/or updated. That is, in at least one example, the rules and/or thresholds can be intelligently determined and/or updated over time, for example via machine-learning mechanisms. In at least one example, a rule can be associated with information that is relevant (e.g., of particular interest) to a partner and/or other entity (e.g., an administrator, etc.). For instance, a rule can be associated with a specified criterion (e.g., age, height, weight, number of dependents, etc.). Additionally, a threshold, which can be used to determine an extent of change that is determined to be permissible (e.g., to a portion of a database storing eligibility data associated with subscriber(s), between a new data file and a previously validated data file, etc.), can be particular to a sponsor and/or a data file. For the purpose of this discussion, an extent of change can be a percentage or other metric that can be used to represent change. In at least one example, such an extent can correspond to a number, a percentage, or other metric of records associated with a specified criterion.

In an example, techniques described herein can receive, at the computing system(s), a new data file, analyze the new data file to identify change(s) to be implemented by the new data file (e.g., determine to what extent a portion of a database storing eligibility data associated with subscriber(s) will change based on the new data file, determine an extent of change between the new data file and a previously validated data file, etc.), and validate the new data file based on comparing the change(s) to a threshold for a particular rule. For the purpose of this discussion, a data file can be valid if the change to be implemented by the data file is less than a threshold associated with each rule that is relevant to the data file. In some examples, all rules in a rule database can be relevant to the data file. In other examples, a subset of rules (or no rules) in the rule database can be relevant to the data file. The relevant rules can be determined based on the sponsor associated with the data file and/or the benefit plan offered by the sponsor. In at least one example, a data file can be invalid if the change to be implemented by the data file meets or exceeds at least one threshold associated with a rule that is relevant to the data file.

As described herein, rules and/or thresholds can be dynamic. That is, rule(s) can change over time depending on what information is relevant to partners, administrators, and/or other entities, and/or based on other variables (e.g., error detection, etc.). In at least one example, new rules can be generated based at least in part on a data model, which can be trained by a machine learning mechanism, as described herein. Additionally, threshold(s) can change over time based on variables associated with data file submissions. For instance, techniques described herein can be directed to learning what percentage (or other metric) of change is expected with certain variables (e.g., geolocations, business domain, business size, business attrition rate, time of month, time of year, season, etc.), and dynamically adjusting a threshold based on such percentage (or other metric). In at least one example, an appropriate threshold can be determined by a data model, which can be trained by a machine learning mechanism, as described herein. In other examples, agent(s) of an administrator can manually manipulate rules and/or thresholds.

As a non-limiting example, a plurality of subscribers can elect a particular benefit plan. The benefit plan can be offered by a sponsor. The benefits offered by the benefit plan, and the specified criteria for receiving such benefits, can be determined by one or more partners. A first partner can indicate that characteristics such as age, plan start date, plan end date, and geographic location are relevant to determining eligibility of benefits offered by the first partner. A second partner can indicate that characteristics such as age, plan start date, plan end date, and the number of alcoholic beverages consumed per day are relevant to determining eligibility of benefits offered by the second partner. A third partner can indicate that characteristics such as age, plan start date, and plan end date are relevant to determining eligibility of benefits offered by the third partner.

Based on the foregoing, the computing system(s) associated with the administrator can determine (e.g., select or generate) a plurality of rules, including but not limited to: a first rule indicating that a validation system shall review data associated with age, a second rule indicating that the validation system shall review data associated with plan start dates, a third rule indicating that the validation system shall review data associated with plan end dates, a fourth rule indicating that the validation system shall review data associated with geographic location, a fifth rule indicating that the validation system shall review data associated with alcoholic beverage consumption, and so forth. Each rule can be associated with a threshold indicating an extent of change (e.g., percentage or other metric) that is permitted given particular variables (e.g., circumstances, determinations, etc.). That is, a threshold can indicate an extent to which data associated with a characteristic corresponding to a rule (that is stored in a database storing eligibility data associated with subscriber(s)) is permitted to change responsive to a new data file. The threshold can be particular to the sponsor and can change based on variables associated with a particular data file. For instance, a threshold for change associated with the second rule (e.g., start dates) may be higher in December, when new plan elections are taking place, than in June, when new plan elections are rare. That is, in at least one example, the threshold can be particular to the sponsor and/or the particular data file. As described above, the threshold can be determined utilizing a data model (which can be trained via a machine-learning mechanism) and/or can be set by an agent associated with the administrator.

The computer system(s) associated with the administrator can receive a new data file from the sponsor. The computing system(s) can analyze the new data file to identify changes to be implemented in a database storing eligibility data associated with a plurality of subscribers by the new data file and/or changes between the new data file and a previously validated data file, and validate the new data file based on comparing the changes to a threshold for each of the rules. The computing system(s) can validate the new data file so long as the changes to data associated with age that are to be implemented by the new data file are less than the threshold associated with the first rule, changes to data associated with start dates are less than the threshold associated with the second rule, changes to data associated with end dates are less than the threshold associated with the third rule, changes to data associated with geographic location are less than the threshold associated with the fourth rule, changes to data associated with alcohol consumption are less than the threshold associated with the fifth rule, and so forth. That is, the computing system(s) can evaluate the new data file in view of the rule(s) relevant to the new data file to determine whether the new data file is valid. If the new data file is validated, the computing system(s) can add the new data file to the database(s). If the changes to be implemented by the new data file meet or exceed one of the thresholds, in some examples, the computing system(s) can determine that the new data file has too many errors and can flag and/or route the data file to an error handling system, which can resolve the error and/or further route the data file to an agent of the administrator and/or the partner that submitted the file.

For instance, as a non-limiting example, a database storing eligibility data associated with a plurality of subscribers can store, in addition to other information, data indicating a start date for benefit plan(s) elected by the plurality of subscribers. If updating the database based on the data file would cause 45% of the start dates to change, and the threshold for change is 25%, the computing system(s) can determine that the new data file has too many errors and can flag and/or route the data file to an error handling system, which, as described above, can resolve the error and/or further route the data file to an agent of the administrator and/or the partner that submitted the file.

Techniques described herein provide numerous improvements to existing technologies. For instance, as a result of implementing the techniques described herein, file-level errors can be detected and remedied more accurately, more rapidly, and often more cost effectively to maintain accurate eligibility data. That is, learning particular types of file-level errors and flagging such errors at the time of submission can enable file-level errors to be identified and remedied to correct erroneous data at the time of submission rather than causing various downstream issues (e.g., patient disruption when accessing care (which can prevent patients from accessing care in times of need) and/or data loss (which can limit information available for building health and/or other benefit plans)) or business and/or legal risk associated with improperly processing claims. As such, techniques described herein significantly improve upon existing eligibility management and/or processing technologies.

Additionally, administrators can improve the efficiency and scalability of managing flexible and responsive healthcare and/or other benefit plans for sponsors utilizing techniques described herein. Moreover, techniques described herein can detect errors and/or changes in data files in near real time, and can notify subscribers, sponsors, partners, and/or other entities (e.g., healthcare providers, etc.) of such peculiarities, without manual intervention. Further, techniques described herein can proactively identify problems with eligibility data and can redress the problems before such problems affect patients or providers at the point of service or other data management.

Furthermore, implementation of the techniques described herein can reduce the number of computational resources consumed by computing systems handling operations for administrators, subscribers, sponsors, partners, and/or other entities (e.g., healthcare providers, etc.) for ensuring data accuracy. By reducing the computational resources consumed by computing system(s) handling operations for an administrator and validating data files such to provide a centralized source of truth, other computing systems handling operations for subscribers, sponsors, partners, and/or other entities (e.g., healthcare providers, etc.) can re-allocate computational resources currently directed to error handling to other computing tasks (which can enable potential direct and indirect cost savings and operational efficiencies). Furthermore, techniques described herein can reduce data transmissions between computing systems handling operations for administrators, subscribers, sponsors, partners, and/or other entities (e.g., healthcare providers, etc.) that are directed to identifying and remedying errors in data files associated with eligibility data.

While this disclosure is directed to error detection and handling with respect to data files associated with eligibility data, techniques described herein can be applicable to various other error-prone data sets. For instance, techniques described herein can be used to validate subscriber and partner utilization and engagement data, plan accounting reconciliation reports, claims data, provider data, etc. In such examples, the databases described below can store different records and/or files, depending on the type of incoming data (to be validated). Nevertheless, in such examples, rules and/or thresholds can be determined for the particular data sets, and can be used to validate incoming data to ensure data accuracy.

FIG. 1 illustrates a system 100 for facilitating intelligent file-level validation. In at least one example, the system 100 includes sponsor computing device(s) 102 operated by sponsor(s) that are in communication with server(s) 104, via network(s) 106. The server(s) 104 can be associated with an administrator, as described above. In at least one example, the server(s) 104 can additionally be in communication with partner computing device(s) 108 operated by partner(s), via the network(s) 106. In additional and/or alternative examples, the server(s) 104 can be in communication with computing device(s) operated by other entities (e.g., health care providers, etc.), which are not shown in FIG. 1.

In at least one example, the sponsor computing device(s) 102 can correspond to a smart phone, a personal digital assistant, a netbook, a laptop computer, a sensor, a networked computing device, and/or another device, which can be capable of transmitting or receiving data directly or via one or more intermediary devices and/or services. In at least one example, the sponsor computing device(s) 102 send data file(s), such as data file 110, to the server(s) 104. In some examples, the data file(s) can be in a text format (e.g., .txt). In at least one example, the data file 110 can identify one or more subscribers 112 and data (e.g., characteristics) associated with the one or more subscribers. For instance, the data file 110 can include a dataset of characteristics associated with one or more subscribers. That is, the data file 110 can identify at least one subscriber and include demographic information (e.g., date of birth, number of dependents, address, etc.) associated with the at least one subscriber, sponsorship information (e.g., employer, length of employment, covered dependents, etc.) associated with the at least one subscriber, plan information (e.g., plan(s) elected, length of election, start date, end date, etc.) associated with the at least one subscriber, etc. In examples where the data file 110 is associated with data corresponding to a plurality of subscribers 112, the data file 110 can include such information for each of the subscribers 112.

In at least one example, the partner computing device(s) 108 can correspond to a smart phone, a personal digital assistant, a netbook, a laptop computer, a sensor, a networked computing device, and/or another device, which can be capable of transmitting or receiving data directly or via one or more intermediary devices and/or services. In at least one example, the server(s) 104 and the partner computing device(s) 108 can exchange data relating to healthcare plans, eligibility, healthcare claims, etc. For instance, in at least one example, the partner computing device(s) 108 can send specified data 114 to the server(s) 104. In some examples, the partner computing device(s) 108 can send specified data 114 at a regular frequency. In other examples, the partner computing device(s) 108 can send specified data 114 in a specification and can subsequently send updates to the specification and/or the data. The specified data 114 can identify one or more characteristics (e.g., criterion) associated with a subscriber 112 receiving benefit(s) from the partner. For instance, a partner can provide specified data 114 that can indicate that a subscriber 112 must have blonde hair, must have a residency in the state of California, and must have been employed by their current employer for more than six months, in order to receive benefits from the partner. In some examples, the one or more characteristics can be identified by another entity (e.g., an administrator, etc.).

The server(s) 104 can be any type of server, such as a network-accessible server. In some examples, the server(s) 104 can be stand-alone computing systems, distributed-computing systems, networked-computing systems, cloud storage, etc. For instance, in at least one example, one or more functionalities described herein as being performed by the server(s) 104 can be performed by a single device or multiple devices. In some examples, one or more functionalities described herein can be performed by one or more remotely located devices instead of, or in addition to, the server(s) 104. That is, in at least one example, the server(s) 104 can offer distributed processing similar to those provided via services, including, but not limited to, seti@home, folding@home, etc.

In at least one example, the server(s) 104 can include processor(s) 116 and computer-readable media 118. The processor(s) 116 can represent, for example, a central processing unit (CPU)-type processing unit, a graphics processing unit (GPU)-type processing unit, a Field-Programmable Gate Array (FPGA), another class of Digital Signal Processor (DSP), or other hardware logic components that can, in some instances, be driven by a CPU. For example, and without limitation, illustrative types of hardware logic components that can be used include Application-Specific Integrated Circuits (ASICs), Application-Specific Standard Products (ASSPs), System-on-a-Chip Systems (SOCs), Complex Programmable Logic Devices (CPLDs), etc. In at least one example, an accelerator can represent a hybrid device, such as one from ZYLEX or ALTERA that includes a CPU course embedded in an FPGA fabric. In various embodiments, the processor(s) 116 can execute one or more modules and/or processes to cause the server(s) 104 to perform a variety of functionalities, as set forth above and explained in further detail in the following disclosure. Additionally, each of the processor(s) 116 can possess its own local memory, which also can store program modules, program data, and/or one or more operating systems. In at least one example, some or all of the computation can be offloaded to a remote processing service (e.g., one or more of the processor(s) can be virtualized).

Depending on the exact configuration and type of the server(s) 104, the computer-readable media 118, can include computer storage media and/or communication media.

Computer storage media can include volatile memory, nonvolatile memory, and/or other persistent and/or auxiliary computer storage media, removable and non-removable computer storage media implemented in any method or technology for storage of information such as computer readable instructions, data structures, program modules, or other data. Computer memory is an example of computer storage media. Thus, computer storage media includes tangible and/or physical forms of media included in a device and/or hardware component that is part of a device or external to a device, including but not limited to random-access memory (RAM), static random-access memory (SRAM), dynamic random-access memory (DRAM), phase change memory (PRAM), read-only memory (ROM), erasable programmable read-only memory (EPROM), electrically erasable programmable read-only memory (EEPROM), flash memory, compact disc read-only memory (CD-ROM), digital versatile discs (DVDs), optical cards or other optical storage media, miniature hard drives, memory cards, magnetic cassettes, magnetic tape, magnetic disk storage, magnetic cards or other magnetic storage devices or media, solid-state memory devices, storage arrays, network attached storage, storage area networks, hosted computer storage or any other storage memory, storage device, and/or storage medium that can be used to store and maintain information for access by a computing device.

In at least one example, the computer storage media can include non-transitory computer-readable media. Non-transitory computer-readable media can include volatile and nonvolatile, removable and non-removable tangible, physical media implemented in technology for storage of information, such as computer readable instructions, data structures, program modules, or other data. The computer-readable media 118 is an example of non-transitory computer-readable media. Non-transitory computer-readable media include, but are not limited to, RAM, ROM, EEPROM, flash memory or other memory technology, CD-ROM, DVDs or other optical storage, magnetic cassettes, magnetic tape, magnetic disk storage or other magnetic storage devices, or any other tangible, physical medium which can be used to store the desired information and which can be accessed by the server(s) 104. Any such non-transitory computer-readable media can be part of the server(s) 104.

In contrast, communication media includes computer readable instructions, data structures, program modules, or other data in a modulated data signal, such as a carrier wave, or other transmission mechanism. As defined herein, computer storage media does not include communication media.

The computer-readable media 118 can include one or more modules and data structures including, for example, an electronic data interchange (EDI) module 120, a database management module 122, a validation module 124, an error handling module 126, a rule generation module 128, and a threshold determination module 130. Additionally, in some examples, the one or more modules and data structures can include one or more databases, such as a record database 132, a file database 134, and a rule database 136. The one or more modules and data structures can be in the form of stand-alone applications, productivity applications, an operating system component, or any other application, software or hardware module configured to facilitate intelligent file-level validation, as described herein.

In at least one example, the EDI module 120 can receive, or otherwise access, data files, such as the data file 110. The EDI module 120 can transform the data file 110 into a particular computer-readable format, such as, but not limited to, JSON, and can send the data file 110 to the database management module 122. For instance, the EDI module 120 can transform the data file 110 from a text format (.txt) to a JSON format and can send the data file 110 to the database management module 122 for processing. The EDI module 120 is not limited to text formats and/or JSON formats, and a variety of format transformations are contemplated herein.

The database management module 122 can manage the one or more databases. For instance, the database management module 122 can add, edit, and/or delete data stored in the one or more databases. In at least one example, the database management module 122 can perform pre-processing on the data file 110 (e.g., in a converted or unconverted format, as discussed above) before the data file 110 is added to any of the one or more databases and/or is sent to the validation module 124 for additional processing.

In at least one example, the record database 132 can store data associated with individual persons (e.g., eligibility data). For instance, a record in the record database 132 can be associated with demographic information associated with a person (e.g., name, age, address, social security number (SSN), etc.), sponsorship information associated with the person (e.g., employer, length of employment, covered dependents, etc.), plan information associated with the person (e.g., plan(s) elected, length of election, start date, end date, etc.), etc. That is, a record in the record database 132 can be a snapshot of a particular person (as defined by one or more characteristics associated with that person) at a particular time. For the purpose of this discussion, one or more persons can be associated with a same subscriber. For instance, a single subscriber can represent an employee and one or more of his/her dependents. As such, one or more records in the record database 132 can be associated with the same sponsorship information and/or plan information, which can be determined based on the subscriber. In alternative examples, a record can be associated with demographic information associated with more than one person (e.g., a married couple, a family, etc.). In at least one example, records stored in the record database 132 can serve as the source of truth for sponsor(s) and/or partner(s).

The file database 134 can store data files. That is, the file database 134 can store raw data files received (and transformed) by the EDI module 120. Each data file in the file database 134 can be associated with a dataset of characteristics associated with a plurality of subscribers. The file database 134 can additionally store information derived from the raw data files. For instance, the file database 134 can store information (e.g., modification data, described below) indicating changes between individual data files in the file database 134 and/or changes associated with the record database 132 responsive to receiving new data files. Furthermore, the file database 134 can store an indication whether a particular data file was added to, or otherwise used to modify, the record database 132 (e.g., due to a determination that the particular data file is valid) or not added to, or otherwise used to modify, the record database 132 (e.g., due to a determination that the particular data file is invalid). In some examples, the file database 134 can store indications of which rule(s) and threshold(s) a particular data file violated (or not) and/or how such a data file was processed via error handling (or not).

The rule database 136 can store one or more rules. In some examples, the rules can be generated based on information that is important to the partner(s), as determined from data associated with specified data 114 provided by the partner(s). That is, a rule can pertain to demographic information (e.g., date of birth, number of dependents, address, etc.), sponsorship information (e.g., employer, length of employment, covered dependents, etc.), plan information (e.g., plan(s) elected, length of election, start date, end date, etc.), etc. In some examples, the rules can be generated based on information that is important to an administrator and/or another entity, or based on other variables (e.g., error detection, etc.). In at least one example, the rules can be configurable and, in some examples, new rules can be added using data models and/or one or more metrics, as described below. In at least one example, rules can be learned over time. In some examples, the data models can be trained via a machine learning mechanism, and can be utilized to determine rules and/or update rules over time. That is, in some examples, rules can be intelligently added and/or modified over time, as described below with reference to the rule generation module 128.

Each rule can be associated with a threshold, which can be used to determine whether a new data file that affects change to individual records and/or the record database 132 should be used to update the record database 132. A threshold can indicate an amount of change that is permissible for data associated with the characteristic corresponding to the rule to which the threshold corresponds. For instance, a threshold can indicate a percentage (or other metric) of records that are permitted to change based on a particular data file.

In at least one example, a threshold for a rule can be particular to a sponsor. That is, in some examples, a rule can be applicable to multiple partners, and each sponsor can be associated with a particular threshold for that rule. In some examples, a threshold can be particular to a sponsor and a sponsor service provider (e.g., a service provider with whom a sponsor contracts for particular services). That is, in some examples, a rule can be associated with multiple thresholds that correspond to a sponsor, each can then be associated with a particular sponsor-sponsor service provider pair. In other examples, a threshold can be associated with a particular sponsor service provider that can be associated with multiple sponsors.

In some examples, the thresholds can be determined based on attribute(s) associated with the sponsor (e.g., geographic location, business domain, business size, attrition rate, etc.), attribute(s) associated with a sponsor service provider, attribute(s) associated with a partner, attribute(s) associated with a record and/or set of record(s), a time of day, a time of month, a time of year, a season, etc. In at least one example, the thresholds can be determined using data models and/or machine learning mechanisms, as described below. In some examples, the thresholds can change dynamically based on variables associated with the receipt of a data file, such as attribute(s) associated with the sponsor (e.g., geographic location, business domain, business size, attrition rate, etc.), attribute(s) associated with a sponsor service provider, attribute(s) associated with a partner, attribute(s) associated with a record and/or set of record(s), a time of day, a time of month, a time of year, a season, etc. That is, in such examples, thresholds can be particular to sponsor(s) and/or data file(s). In at least one example, a threshold can be equal to zero, indicating that change is not permissible for a corresponding characteristic. In at least one example, a threshold can be equal to one (e.g., on a scale from zero to one), 100% (e.g., on a scale from 0%-100%), etc., indicating that any amount of change is permissible for a corresponding characteristic. A threshold can be any percentage (or other metric) between the two extremes.

While the record database 132, the file database 134, and the rule database 136 are depicted in FIG. 1 as three separate databases, in an alternate example, data stored in such databases can be stored in one database, two databases, or any number of individual databases.

It should be noted that techniques described herein can be applicable to various other error-prone data sets. For instance, techniques described herein can be used to validate subscriber and partner utilization and engagement data, plan accounting reconciliation reports, claims data, provider data, etc., as described above. In such examples, the record database 132 can store different records and/or the file database 134 can store different files, depending on the type of incoming data that is being validated. Additionally, the rule(s) stored in the rule database 136 can change such to be particular to the incoming data that is being validated.

As described above, in at least one example, the database management module 122 can perform pre-processing on the data file 110 before the data file 110 is added to any of the one or more databases and/or is sent to the validation module 124 for additional processing. In at least one example, the database management module 122 can receive a data file 110 and can analyze the data file 110 based on one or more criteria to determine whether to add the data file 110 to the file database 134. For instance, the database management module 122 can analyze the data file to ensure that the data file 110 is not corrupt, or is otherwise not readable (e.g., if a subscriber appears multiple times in a same file). Additional and/or alternative criteria can be used to determine whether to add the data file 110 to the file database 134. In at least one example, based at least in part on determining that the data file 110 satisfies the one or more criteria, the database management module 122 can add the data file 110 to the file database 134. Based at least in part on determining that the data file 110 does not satisfy the one or more criteria, the database management module 122 can send the data file 110 to the error handling module 126 and can refrain from adding the data file 110 to the file database 134.

Based at least in part on adding the data file 110 to the file database 134, the database management module 122 can determine modification data that is indicative of change caused by the addition of the data file 110 to the file database 134. In at least one example, the database management module 122 can compare the data file 110 to one or more data files stored in the file database 134 and can determine one or more changes between the data file 110 and the one or more data files stored in the file database 134. For instance, the database management module 122 can compare a first dataset associated with one or more characteristics of a plurality of subscribers that is associated with the data file 110 with a second dataset associated with one or more characteristics of a plurality of subscribers that is associated with a previously validated data file stored in the file database 134. That is, the modification data can indicate changes between the data file 110 and one or more previously successful comparable data files (e.g., file-level changes). In at least one example, the modification data can indicate, for each characteristic, a percentage (or other metric) of records changed based on a new data file. Additionally and/or alternatively, the database management module 122 can determine how the data file 110 would change the record database 132 if the data file 110 were added to the record database 132. In at least one example, the modification data can indicate, for each characteristic, a percentage (or other metric) of records in the record database 132 to be changed based on a new data file. That is, the modification data can indicate database-level changes. Accordingly, the modification data can represent file-level change(s) and/or database-level change(s). Data indicating the change (e.g., modification data) implemented by the data file 110 can be stored in the file database 134.

The validation module 124 can utilize the modification data to determine whether the data file 110 is to be added to the record database 132. That is, the validation module 124 can analyze a new data file, such as data file 110, and modification data associated with the data file 110 to determine whether change(s) to be implemented by the data file 110 are acceptable (or not). In at least one example, the validation module 124 can access a rule from the rule database 136 and can determine the appropriate threshold for the rule. In at least one example, the appropriate threshold is based on the sponsor associated with the data file 110. Additionally and/or alternatively, the appropriate threshold can be determined based on attribute(s) associated with the sponsor (e.g., geographic location, business domain, business size, attrition rate, etc.), attribute(s) associated with a sponsor service provider, attribute(s) associated with a partner, attribute(s) associated with a record and/or set of record(s), a time of day, a time of month, a time of year, a season, etc. That is, the appropriate threshold can be dynamic and can change based on variables associated with the submission of the data file 110.

In at least one example, the validation module 124 can compare the modification data with the threshold, to determine how the change to be implemented by the data file 110 (e.g., to the portion of the record database 132 associated with the characteristic to which the rule pertains, to the portion of a previously validated data file associated with the characteristic to which the rule pertains, etc.) relates to the threshold. For instance, in an example, the validation module 124 can compare a first amount of change (e.g., percentage or other metric) that would result should the data file 110 be used to update the record database 132 with a second amount of permissible change (e.g., percentage or other metric) as defined by a particular threshold. Additionally and/or alternatively, the validation module 124 can compare a first amount of change (e.g., percentage or other metric) between the data file 110 and a previously validated data file with a second amount of permissible change (e.g., percentage or other metric) as defined by a particular threshold. In at least one example, the validation module 124 can utilize one or more similarity algorithms to determine how the first amount of change compares to a particular threshold. Such similarity algorithms can utilize Euclidean distance, Manhattan distance, Minkowski distance, Cosine similarity, Jaccard similarity, etc. to determine whether the first amount of change meets or exceeds a particular threshold. Based on determining that the change to be implemented by the data file 110 is below the threshold, the validation module 124 can determine that the data file 110 satisfies the rule.

The validation module 124 can repeat the same process for each rule, and respective threshold, that is relevant to the data file 110. In some examples, all of the rules in the rule database 136 can be determined to be relevant to the data file 110. In other examples, a subset of rules in the rule database 136 can be determined to be relevant to the data file 110. In such examples, the subset of rules (or no rules) can be determined based on the sponsor and/or benefit plan associated with the data file 110. For example, the subset of rules can be determined by specified criteria defined by partner(s) associated with a sponsor associated with a data file. In some examples, the validation module 124 can compare the modification data with a single rule at one time. In other examples, the validation module 124 can compare the modification data with multiple rules at the same time (e.g., in parallel).

If the data file 110 satisfies each rule (that is, the change is less than each respective threshold) that is applicable for the data file 110, the validation module 124 can validate the data file 110 and can send an instruction to the database management module 122 to update the record database 132 based at least in part on the data file 110. Responsive to receiving the instruction to update the record database 132, the database management module 122 can add the data file 110 to the record database 132 and/or update the record database 132 to include information from the data file 110.

Based on determining that the change to be implemented by the data file 110 meets or exceeds the threshold, the validation module 124 can determine that the data file 110 may not be valid and, in some examples, can send the data file 110 to the error handling module 126. In some examples, the validation module 124 can analyze each rule that is applicable for the data file 110 and, if the data file 110 does not satisfy a particular rule, the validation module 124 can route the data file 110 to the error handling module 126. In other examples, the validation module 124 can analyze the data file 110 in view of all of the applicable rules prior to determining whether to route the data file 110 to error handling. That is, in such examples, after analyzing all of the rules that are applicable to a data file 110, the validation module 124 can identify which rule(s) the data file 110 did not satisfy, and can determine how to route the data file 110 based on the rule(s) that the data file 110 did not satisfy.

In at least one example, the validation module 124 can generate data indicating whether the data file 110 is valid and/or which rule(s) the data file 110 did not satisfy. Moreover, in some examples, the validation module 124 can generate data indicating relationship(s) between the data file 110 and relevant threshold(s) (e.g., a value indicating an extent that the change exceeded a threshold, an extent that the change was below a threshold, etc.). In some examples, such data can be stored in association with the data file 110 in the file database 134.

In at least one example, responsive to receiving a data file 110, the error handling module 126 can send a notification to the sponsor computing device(s) 102 to notify the sponsors that the data file 110 likely includes an error. In other examples, the error handling module 126 can send the data file 110 to a queue for manual review by a human analyst (e.g., an agent associated with the administrator). In such examples, the human analyst can override the errors if he/she determines that the data file 110 is valid. In both examples, the sponsor or the human analyst can identify and remedy the error.

In additional and/or alternative examples, the server(s) 104 can receive data from the partner computing device(s) 108 and/or other sources and/or systems (e.g., healthcare provider computing device(s), etc.) and the error handling module 126 can analyze the data to determine whether the data file 110 does in fact include an error. For instance, the error handling module 126 can compare healthcare provider bills, records of services provided to subscribers, claims submissions, etc. to determine if a change included in the data file 110 is accurate. As a non-limiting example, the data file 110 can indicate that a start date for a plurality of subscribers changed from January 1 to July 1. However, the error handling module 126 can access healthcare provider bills, records of services provided to subscribers, claims submissions, etc. that are associated with services prior to July 1. Accordingly, the error handling module 126 can determine that the change indicated by the file is erroneous and can refrain from modifying the record database 132 based on the data file 110. In such an example, the error handling module 126 can send a notification to the sponsor indicating that the data file 110 included errors, identifying the errors, and notifying the sponsor that the errors have been corrected, if applicable.

The error handling module 126 can handle additional and/or alternative errors as well. For instance, based on the database management module 122 determining that the data file 110 does not meet the one or more criteria, as described above, the database management module 122 can send the data file 110 to the error handling module 126. In at least one example, the error handling module 126 can send a notification to the sponsor computing device(s) 102 to notify the sponsors that the data file 110 does not satisfy the one or more criteria. In other examples, the error handling module 126 can send the data file 110 to a queue for manual review by a human analyst. In such examples, the human analyst can override the errors if he/she determines that the data file 110 satisfies the one or more criteria. Or, the human analyst can identify and remedy the error(s).

In some examples, one or more rules can be weighted. That is, in some examples, a first rule can be weighted with a weight (e.g., zero or near zero) indicating that failure of the first rule does not warrant routing a data file 110 to the error handling module 126. In such examples, the first rule can be flagged as a failure (when appropriate) and the data file 110 can still be used to update the rule database 136. Such flagging can be useful for learning rules and/or thresholds. In other examples, a second rule can be weighted with a weight (e.g., one or near one) indicating that failure of the second rule invalidates the entire data file 110 and/or causes the data file 110 to be routed directly to the error handling module 126. Accordingly, in some examples, the validation module 124 can leverage weight(s) associated with rule(s) to determine whether to route a data file 110 to the error handling module 126 or to send an instruction to the database management module 122 to cause the data file 110 to be added to the record database 132.

In some examples, a result from the error handling module 126 can be used in part to train a machine learning mechanism to more accurately determine how to set a threshold, as described below with reference to FIG. 5, and/or when to determine that a data file is valid or invalid, as described below with reference to FIG. 6. Furthermore, in at least one example, results from the error handling module 126 can be used in part to determine that a rule and/or threshold is incorrect. For instance, in at least one example, a number of data files can be determined to be invalid due to change(s) exceeding threshold(s) of rule(s). In examples where the number of data files determined to be invalid meets or exceeds a threshold (different than the thresholds associated with rules described above), the error handling module 126 can flag the rule(s) and/or threshold(s) causing the data files to be invalid and can cause such rule(s) and/or threshold(s) to be reviewed for accuracy. Similarly, in at least one example, a number of data files from a same sponsor can be determined to be invalid due to change(s) exceeding threshold(s) of rule(s). In examples where the number of data files determined to be invalid meets or exceeds a threshold (different than the thresholds associated with rules described above), the error handling module 126 can flag the sponsor to initiate a review process associated with the sponsor. In some examples, such observations can be utilized to determine how to weight rule(s), as described above.

The rule generation module 128 can be configured to generate new rules that can be added to the rule database 136. As described above, the rules can be determined based on information that is important to the partner(s), as determined from specified data 114 received by the server(s) 104. That is, a rule can pertain to demographic information (e.g., date of birth, number of dependents, address, etc.), sponsorship information (e.g., employer, length of employment, covered dependents, etc.), plan information (e.g., plan(s) elected, length of election, start date, end date, etc.), etc. In some examples, the rule generation module 128 can occasionally (e.g., at a particular frequency, after a lapse in a predetermined period of time, responsive to receiving new data, after a new partner computing device 108 is added, etc.) analyze specified data 114 received by partner(s) to determine when new information (e.g., new criterion) is of interest to the partners. In at least one example, the rule generation module 128 can receive specified data 114 and analyze the specified data 114 to determine whether the rule database 136 includes a rule for each criterion specified in the specified data 114. If the rule database 136 does not include a rule for a criterion, the rule generation module 128 can generate a new rule. That is, based at least in part on determining new information is of interest, the rule generation module 128 can generate a new rule for such information and can store the new rule in the rule database 136. For instance, if Partner A is concerned with age, height, weight, and alcohol consumption and then Partner A becomes concerned with age, height, weight, alcohol consumption, and geographic location, then the rule generation module 128 can generate a new rule associated with geographic location. As described above, in some examples, the rule generation module 128 can add new rules based on information that is important to administrator(s) and/or other entities, and/or based on other variables (e.g., error detection, etc.).

Furthermore, in at least one example, the rule generation module 128 can generate new rules based on a prediction of what might be interesting to the partner(s), administrator(s), and/or other entities. That is, in such examples, the rule generation module 128 can generate new rules that are additional and/or alternative to rule(s) based on specified data 114. Furthermore, in such examples, the rule generation module 128 can leverage specified data associated with partner(s), administrator(s), and/or other entities and/or additional and/or alternative data sources to generate such new rules via machine learning mechanisms described herein.

In some examples, the rule generation module 128 can employ one or more data models and/or can apply one or more metrics to generate new rule(s). Several examples of suitable data models that can be used to determine rule(s) can include regression models, such as linear regression models, and stochastic models, such as Markov models, hidden Markov models, and so forth. Additionally and/or alternatively, various reasoning systems can be utilized to determine rule(s). For instance, the rule database 136 can utilize forward chaining, opportunistic reasoning, or other inference-based methods to determine rule(s).

In some examples, the rule generation module 128 can utilize a machine learning mechanism to build, modify, or otherwise utilize data model(s) that are created from example inputs and makes predictions or decisions. In such an example, the data model(s) may be trained using supervised learning algorithms (e.g., artificial neural networks, Bayesian statistics, support vector machines, decision trees, classifiers, k-nearest neighbor, etc.), unsupervised learning algorithms (e.g., artificial neural networks, association rule learning, hierarchical clustering, cluster analysis, etc.), semi-supervised learning algorithms, deep learning algorithms, etc. In at least one example, the example inputs can include previously received specified data 114, previously stored rule(s), and rule(s) generated responsive to receiving particular specified data 114. In such examples, the rule generation module 128 can build, modify, or otherwise utilize data model(s) to make prediction(s) with respect to rule(s) that might be of interest to the partner(s).

The threshold determination module 130 can be configured to determine thresholds for rules. That is, in at least one example, the threshold determination module 130 can be configured to determine what percentage (or other metric) of change is permissible given certain variables. As described above, each rule can be associated with one or more thresholds. Each threshold can be associated with a particular sponsor, or a sponsor-sponsor service provider pair. The certain variables can be based on attribute(s) associated with a sponsor, including, but not limited to, a geolocation of the sponsor, a business domain of the sponsor, a business size of the sponsor, an attrition rate associated with the sponsor, etc., attribute(s) associated with a partner, attribute(s) associated with a record and/or set of record(s), and/or information associated with the submission of the data file, including, but not limited to, a time of day, a time of month, a time of year, a season, etc. In some examples, the threshold determination module 130 can employ one or more data models and/or can apply one or more metrics to determine a threshold for particular rules. Several examples of suitable data models that can be used to predict a threshold can include regression models, such as linear regression models, and stochastic models, such as Markov models, hidden Markov models, and so forth. Additionally and/or alternatively, various reasoning systems can be utilized to determine threshold(s). For instance, the threshold determination module 130 can utilize forward chaining, opportunistic reasoning, or other inference-based methods to determine threshold(s).

In some examples, the threshold determination module 130 can train a data model via machine learning mechanism(s) to determine what percentage (or other metric) of change is permissible given certain variables. In at least one example, the threshold determination module 130 may utilize a machine learning mechanism to build, modify, or otherwise utilize data model(s) that are created from example inputs and makes predictions or decisions. In such an example, the data model(s) may be trained using supervised learning algorithms (e.g., artificial neural networks, Bayesian statistics, support vector machines, decision trees, classifiers, k-nearest neighbor, etc.), unsupervised learning algorithms (e.g., artificial neural networks, association rule learning, hierarchical clustering, cluster analysis, etc.), semi-supervised learning algorithms, deep learning algorithms, etc. In at least one example, the example inputs can include previously received data files, modification data associated with the data files, attribute(s) associated with particular sponsors, attribute(s) associated with a partner, attribute(s) associated with a record and/or set of record(s), information associated with submission of the data file (e.g., a time of day, a time of month, a time of year, a season, etc.), and indications as to whether the data files were added to the record database 132 (e.g., due to a determination that the particular data file was valid) or not added to the record database 132 (e.g., due to a determination that the particular data file was not valid). Based at least in part on the inputs, the threshold determination module 130 can build, modify, or otherwise utilize data model(s) to make a prediction with respect to an appropriate threshold of change for a particular rule.

As described above, in at least one example, a threshold can be equal to zero, indicating that change is not permissible for a corresponding characteristic. In at least one example, a threshold can be equal to one (e.g., on a scale from zero to one), 100% (e.g., on a scale from 0-100%), etc., indicating that any amount of change is permissible for a corresponding characteristic. In other examples, a threshold can be any percentage (or metric) in between such extremes.

FIGS. 2-6 describe example processes for facilitating intelligent file-level validation. The example processes are described in the context of the system of FIG. 1, but are not limited to those environments.

The processes described above in association with FIGS. 2-6 can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functionalities or implement particular abstract data types. In other embodiments, hardware components perform one or more of the operations. Such hardware components can include or be incorporated into processors, ASICs, programmable circuits such as FPGAs, or in other ways. The order in which the operations are described is not intended to be construed as a limitation, and any number of the described operations and/or processes can be combined in any order and/or in parallel to implement the processes.

Figure 2:
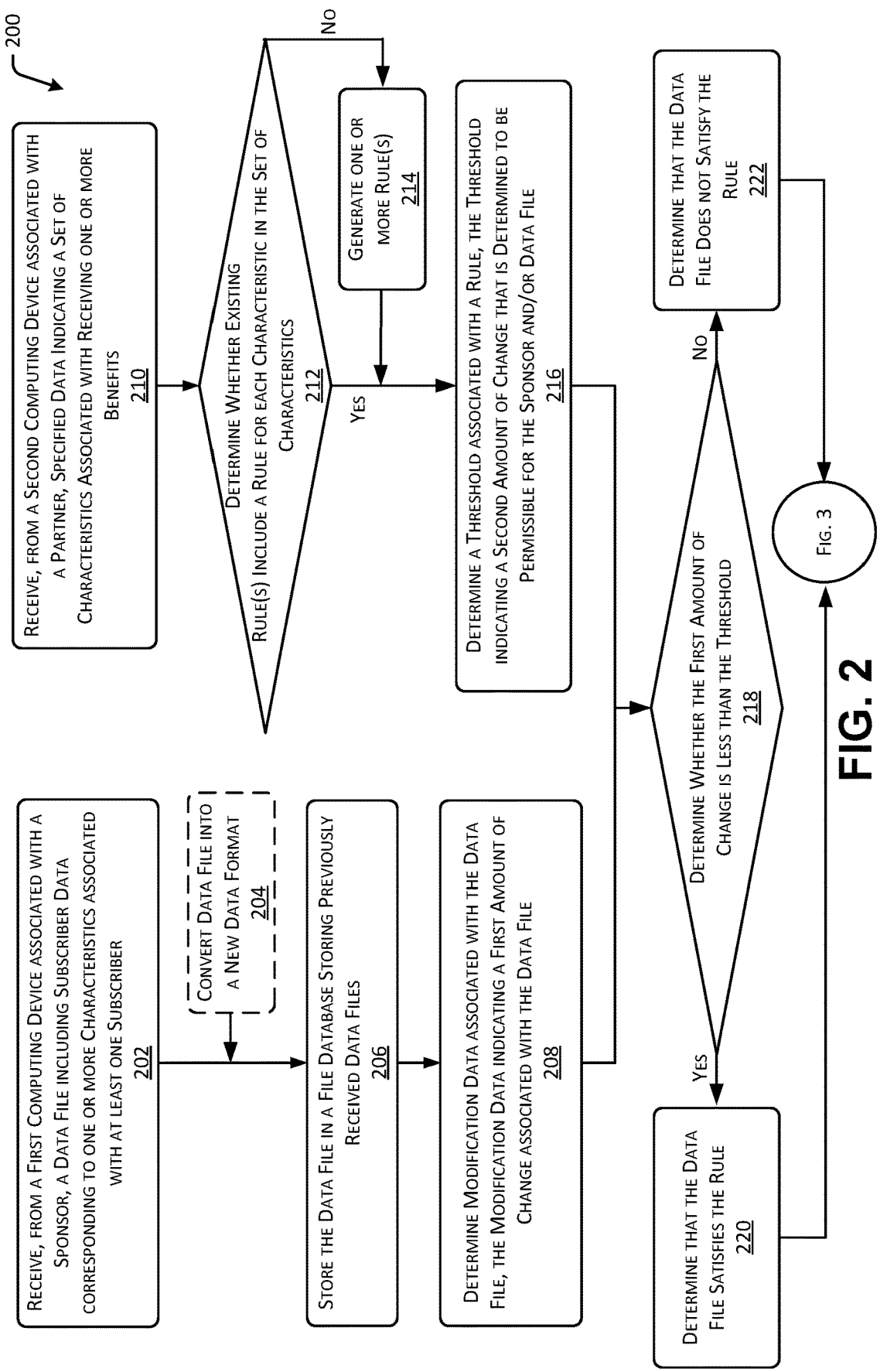
FIG. 2 illustrates an example process for facilitating intelligent file-level validation.

FIG. 2 illustrates an example process 200 for facilitating intelligent file-level validation.

Block 202 illustrates receiving, from a first computing device associated with a sponsor, a data file including subscriber data corresponding to one or more characteristics associated with at least one subscriber. As described above, in at least one example, the sponsor computing device(s) 102 can send data file(s), such as data file 110, to the server(s) 104. In some examples, the data file(s) can be in a text format (e.g., .txt). In at least one example, the data file 110 can identify one or more subscribers 112 and data (e.g., characteristics) associated with the one or more subscribers 112. For instance, the data file 110 can include a dataset of characteristics associated with one or more subscribers. That is, the data file 110 can identify at least one subscriber and include demographic information (e.g., date of birth, number of dependents, address, etc.) associated with the at least one subscriber, sponsorship information (e.g., employer, length of employment, covered dependents, etc.) associated with the at least one subscriber, plan information (e.g., plan(s) elected, length of election, start date, end date, etc.) associated with the at least one subscriber, etc. In examples where the data file 110 is associated with data corresponding to a plurality of subscribers 112, the data file 110 can include such information for each of the subscribers 112.

While block 202 illustrates receiving the data file 110 from the sponsor computing device(s) 102, in additional and/or alternative examples, the server(s) 104 can access the data file 110 locally or from another data source accessible to the server(s) 104.

Block 204, which can be optional in some examples, illustrates converting the data file into a new computer-readable format. In at least one example, the EDI module 120 can receive data files, such as the data file 110. If the data file 110 is in a text format (as is shown in FIG. 1), the EDI module 120 can transform the data file 110 into another computer-readable format, such as, but not limited to, JSON, and can send the data file 110 to the database management module 122. That is, the EDI module 120 can transform the data file 110 from a text format (.txt) to a JSON format and can send the data file 110 to the database management module 122 for processing.

Block 206 illustrates storing the data file in a file database storing previously received data files. As described above, the database management module 122 can manage the one or more databases. For instance, the database management module 122 can add, edit, and/or delete data stored in the one or more databases. In at least one example, the database management module 122 can perform pre-processing on the data file 110 before the data file 110 is added to any of the one or more databases and/or is sent to the validation module 124 for additional processing.

For instance, in at least one example, the database management module 122 can perform pre-processing on the data file 110 before the data file 110 is added to any of the one or more databases and/or is sent to the validation module 124 for additional processing. In at least one example, the database management module 122 can receive a data file 110 and can analyze the data file 110 based on one or more criteria to determine whether to add the data file 110 to the file database 134. In at least one example, based at least in part on determining that the data file 110 satisfies the one or more criteria, the database management module 122 can add the data file 110 to the file database 134.

Block 208 illustrates determining modification data associated with the data file, the modification data indicating a first amount of change associated with the data file. Based at least in part on adding the data file 110 to the file database 134, the database management module 122 can determine modification data that is indicative of change caused by the addition of the data file 110 to the file database 134. In at least one example, the database management module 122 can compare the data file 110 to one or more data files stored in the file database 134 and can determine one or more changes between the data file 110 and the one or more data files stored in the file database 134. For instance, the database management module 122 can compare a first dataset associated with one or more characteristics of a plurality of subscribers that is associated with the data file 110 with a second dataset associated with one or more characteristics of a plurality of subscribers that is associated with a previously validated data file stored in the file database 134. For instance, the modification data can indicate changes between the data file 110 and one or more previously successful comparable data files (e.g., file-level changes). In at least one example, the modification data can indicate, for each characteristic, a percentage (or other metric) of records changed (or to be changed) based on a new data file.

Additionally and/or alternatively, the database management module 122 can determine how the data file 110 would change the record database 132 if the data file 110 were added to the record database 132. In at least one example, the modification data can indicate, for each characteristic, a percentage (or other metric) of records in the record database 132 changed (or to be changed) based on a new data file. That is, the modification data can indicate database-level changes. Accordingly, the modification data can represent file-level change(s) and/or database-level change(s). Data indicating the change (e.g., modification data) implemented by the data file 110 can be stored in the file database 134, as described above.

Block 210 illustrates receiving, from a second computing device associated with a partner, specified data indicating a set of characteristics associated with receiving one or more benefits. As described above, in at least one example, the partner computing device(s) 108 can send specified data 114 to the server(s) 104. The specified data 114 can identify one or more characteristics that are required for a subscriber 112 to receive benefit(s) from the partner. In additional and/or alternative examples, specified data can be determined and/or provided by other entities (e.g., the administrator, etc.).

Block 212 illustrates determining, whether existing rule(s) include a rule for each characteristic in the set of characteristics. In at least one example, the rule generation module 128 can analyze the specified data to determine whether rule(s) in the rule database 136 include rules for each characteristic in the set of characteristics, a plurality of rules. Based at least in part on determining that the rule database 136 does not include rules for each characteristic in the set of characteristics, the rule generation module 128 can generate new rule(s) for each characteristic that does not have a corresponding rule in the rule database 136, as illustrated in block 214. As described above, in at least one example, the rule generation module 128 can utilize data models and/or one or more metrics to add rule(s) to the rule database 136 and/or update the rule database 136. In at least one example, rules can be learned over time. In some examples, one or more data models, which can be trained via a machine learning mechanism, can be utilized to determine rules and/or update rules over time. Additional details are provided below with respect to FIG. 4.

While blocks 210 and 212 are described above with reference to receiving specified data from partner(s), in additional and/or alternative examples, the server(s) 104 can receive specified data from administrator(s) and/or other entities.

Block 216 illustrates determining a threshold associated with a rule, the threshold indicating a second amount of change that is determined to be permissible for the sponsor and/or data file. In at least one example, responsive to determining that the rule database 136 includes rule(s) for each characteristic in the set of characteristics (or generating new rule(s) such that the rule database 136 includes rule(s) for each characteristic in the set of characteristics), the validation module 124 can access a rule from the rule database 136 and can determine the appropriate threshold for the rule. The threshold can indicate a permissible amount (e.g., percentage or other metric) of change that can result from the data file 110. In at least one example, the appropriate threshold is based on the sponsor associated with the data file 110. Additionally and/or alternatively, the appropriate threshold can be determined based on attribute(s) associated with the sponsor (e.g., geographic location, business domain, business size, attrition rate, etc.), attribute(s) associated with a sponsor service provider, attribute(s) associated with a partner, attribute(s) associated with a record and/or set of record(s), a time of day, a time of month, a time of year, a season, etc. associated with the data file 110. That is, in such an example, the threshold can be particular to the data file 110. Additional details associated with determining a threshold are described below with reference to FIG. 5.

Block 218 illustrates determining whether the first amount of change is less than the threshold. In at least one example, the validation module 124 can compare the modification data with the threshold, to determine how the change to be implemented by the data file 110 (file-level and/or database-level) relates to the threshold. For instance, the validation module 124 can determine, for the particular characteristic associated with the rule, whether the percentage of records that would be changed based on the data file 110 is greater than or less than a permissible amount (e.g., percentage or other metric) of change as indicated by the threshold. In at least one example, the validation module 124 can utilize one or more similarity algorithms to determine how the first amount of change compares to a particular threshold, as described above. Based at least in part on the first amount of change being less than a threshold, the validation module can determine that the data file 110 satisfies the rule, as illustrated in block 220, and process 200 can continue via process 300, described below with reference to FIG. 3. Based at least in part on the first amount of change being greater than or equal to the threshold, the validation module 124 can determine that the data file 110 does not satisfy the rule, as illustrated in block 222, and can continue via process 300, descried below with reference to FIG. 3.

Figure 3:
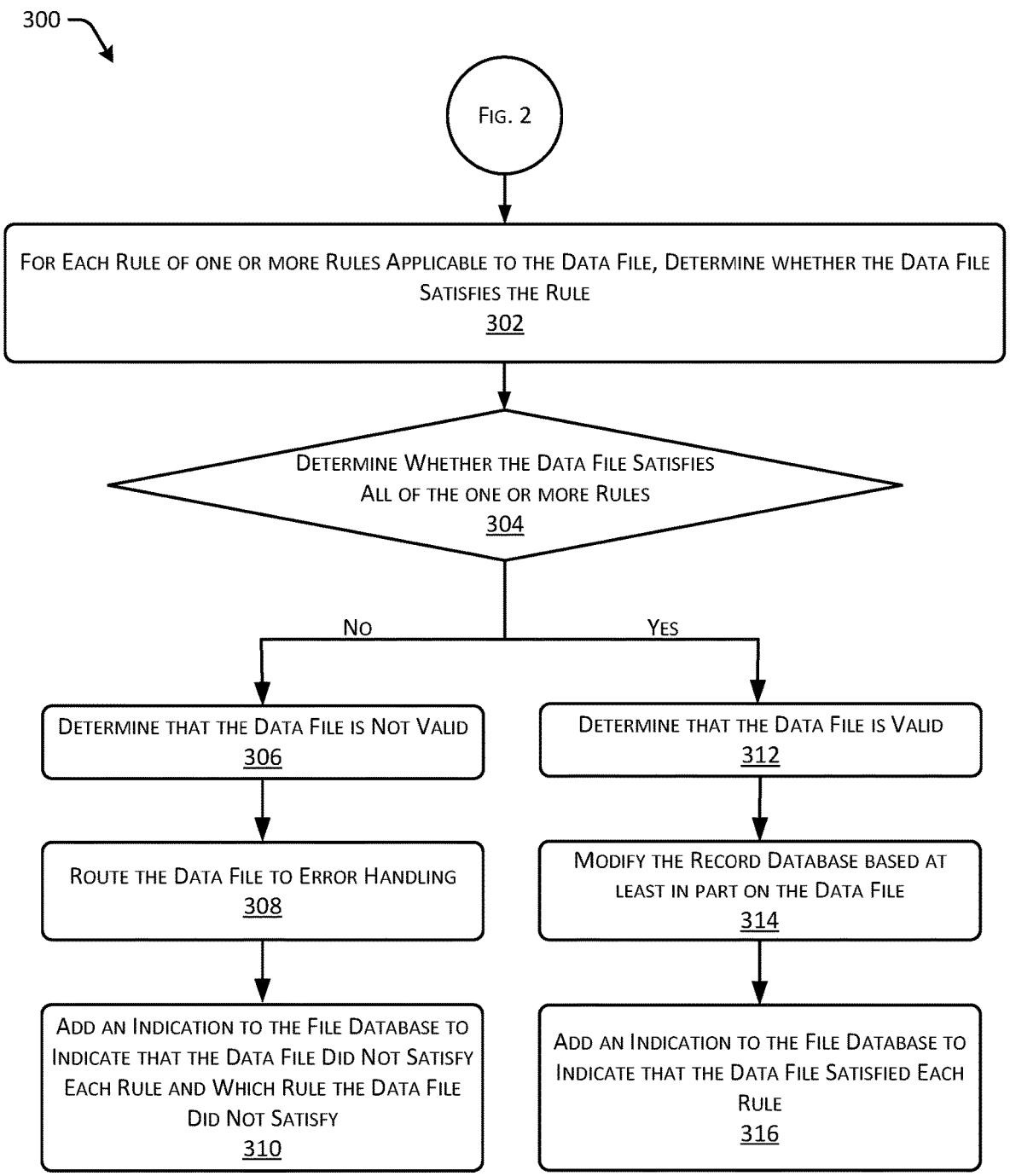
FIG. 3 illustrates additional details associated with the example process for facilitating intelligent file-level validation as described in FIG. 2.

FIG. 3 illustrates additional details associated with facilitating intelligent file-level validation, as shown in process 300.

Block 302 illustrates, for each rule of one or more rules, determining whether the data file satisfies the rule. As described above with respect to FIG. 2, the validation module 124 determines whether a data file 110 satisfies a rule based on how change(s) to be implemented by the data file 110 (file-level or record-level) compare to a threshold associated with the rule. The validation module 124 can repeat the same process for each rule, and respective threshold, that is relevant to the data file 110. In some examples, all of the rules in the rule database 136 can be determined to be relevant to the data file 110. In other examples, a subset of rules (or, no rules) in the rule database 136 can be determined to be relevant to the data file 110. In such examples, the relevant rules can be determined based on the sponsor and/or benefit plan associated with the data file 110 and/or other circumstances associated with the submission of the data file 110. In some examples, the validation module 124 can compare the modification data with a single rule at one time. In other examples, the validation module 124 can compare the modification data with multiple rules at the same time (e.g., in parallel).

Block 304 illustrates determining whether the data file satisfies all of the one or more rules. The validation module 124 can determine whether the data file 110 satisfies all of the rules, or whether the data file 110 failed at least one rule. As described above, in some examples, the validation module 124 can determine whether the data file 110 satisfies all of the rules after the validation module 124 has analyzed the data file 110 in view of all of the rules that are relevant to the data file 110.

Based at least in part on determining that the data file 110 does not satisfy all of the one or more rules (i.e., the data file 110 fails one or more rules), the validation module 124 can determine that the data file 110 may not be valid, as illustrated in block 306. In such examples, the validation module 124 can determine which rule(s) the data file 110 did not satisfy.

Block 308 illustrates routing the data file to error handling. In at least one example, based on determining that the change to be implemented by the data file 110 fails at least one rule, the validation module 124 can determine that the data file 110 may not be valid and can send the data file 110 to the error handling module 126. In at least one example, the error handling module 126 can send a notification to the sponsor computing device(s) 102 to notify the sponsors that the data file 110 likely includes an error. In other examples, the error handling module 126 can send the data file 110 to a queue for manual review by a human analyst. In such examples, the human analyst can override the errors if he/she determines that the data file 110 is valid. Or, the human analyst can identify and remedy the error. In at least one example, action(s) taken by the human analyst (e.g., override, remedy, etc.) can be associated with data, which can be stored in association with the data file 110 in the file database 134.

In additional and/or alternative examples, the server(s) 104 can receive data from the partner computing device(s) 108 and/or other sources and/or systems (e.g., healthcare provider computing device(s), etc.) and the error handling module 126 can analyze the data to determine whether the data file 110 does in fact include an error. For instance, the error handling module 126 can compare healthcare provider bills, records of services provided to subscribers, claims submissions, etc. to determine if a change included in the data file 110 is accurate, as described above. Additional details pertaining to such error handling are described below with reference to FIG. 6.

Block 310 illustrates adding an indication to the file database to indicate that the file did not satisfy each rule and which rule the data file did not satisfy. As described above, the file database 134 can store information derived from raw data files. For instance, the file database 134 can store an indication that the data file 110 was not added to, or otherwise used to modify, the record database 132 (e.g., due to a determination that the particular data file is invalid). In some examples, the file database 134 can store indications of which rule(s) the data file 110 violated and/or how the data file 110 was processed via error handling (or not). In an example where a human analyst overrides the errors, the file database 134 can store an indication of such in association with the data file 110.

Based at least in part on determining that the data file 110 satisfies all of the one or more rules, the validation module 124 can determine that the data file 110 is valid, as illustrated in block 312. That is, if the data file 110 satisfies each rule (that is, the change is less than each respective threshold) that is relevant to the data file 110, the validation module 124 can validate the data file 110.

Block 314 illustrates modifying the record database based at least in part on the data file. Based at least in part on validating the data file 110, the validation module 124 can send an instruction to the database management module 122 to update the record database 132 based at least in part on the data file 110. Responsive to receiving the instruction to update the record database 132, the database management module 122 can add the data file 110 to the record database 132 and/or update the record database 132 to include information from the data file 110.

Block 316 illustrates adding an indication to the file database to indicate that the data file satisfied each rule. As described above, the file database 134 can store information derived from raw data files. For instance, the file database 134 can store an indication that the data file 110 was added to, or otherwise used to modify, the record database 132 (e.g., due to a determination that the particular data file is valid). In some examples, the file database 134 can store an indication that the data file 110 satisfied all of the rules.

Figure 4:
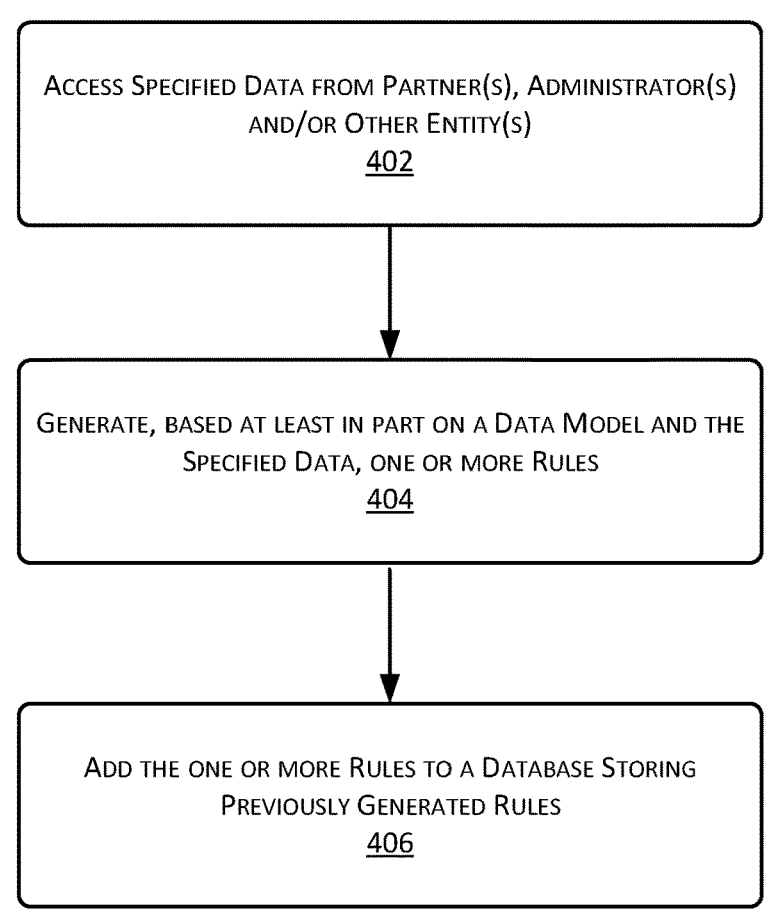
FIG. 4 illustrates an example process for generating and/or updating rule(s) in a rule database.

FIG. 4 illustrates an example process 400 for learning new rules to be added to the rule database 136.

Block 402 illustrates accessing specified data from partner(s), administrator(s), and/or other entity(s). As described above, in at least one example, the partner computing device(s) 108 can send specified data 114 to the server(s) 104. The specified data 114 can identify one or more characteristics that are required for a subscriber 112 to receive benefit(s) from the partner. Additionally and/or alternatively, administrators can specify one or more characteristics that are of interest to the administrators. Additional and/or alternative entities can also provide specified data.

Block 404 illustrates generating, based at least in part on a data model and the specified data, one or more rules. The rule generation module 128 can be configured to generate new rules that can be added to the rule database 136. As described above, the rules can be generated based on information that is important to the partner(s), administrator(s), and/or other entity(s). For instance, the rules can be generated based on specified data 114 received by the server(s) 104, from partner computing device(s) 108. That is, a rule can pertain to demographic information (e.g., date of birth, number of dependents, address, etc.), sponsorship information (e.g., employer, length of employment, covered dependents, etc.), plan information (e.g., plan(s) elected, length of election, start date, end date, etc.), etc. In some examples, the rule generation module 128 can occasionally (e.g., at a particular frequency, after a lapse in a predetermined period of time, responsive to receiving new data, after a new partner computing device 108 is added, etc.) analyze specified data 114 received by partner(s) to determine when new information (e.g., new criterion) is of interest to the partners. Additionally and/or alternatively, the rules can be generated based on specified data associated with administrator(s) and/or other entity(s).

In some examples, the rule generation module 128 can generate new rules based on a prediction of what might be interesting to the partner(s), administrator(s), and/or other entity(s). That is, in such examples, the rule generation module 128 can generate new rules that are additional and/or alternative to rule(s) based on specified data 114, as described above. In such examples, the rule generation module 128 can leverage specified data associated with partner(s), administrator(s), and/or other entities and/or additional and/or alternative data sources to generate such new rules.

In at least one example, the rule generation module 128 can employ one or more data models and/or can apply one or more metrics to determine new rule(s). Several examples of suitable data models that can be used to determine rule(s) can include regression models, such as linear regression models, and stochastic models, such as Markov models, hidden Markov models, and so forth. Additionally and/or alternatively, various reasoning systems can be utilized to determine rule(s). For instance, the rule database 136 can utilize forward chaining, opportunistic reasoning, or other inference-based methods to determine rule(s). In some examples, the rule generation module 128 can utilize a machine learning mechanism to build, modify, or otherwise utilize data model(s) that are created from example inputs and makes predictions or decisions. In such an example, the data model(s) may be trained using supervised learning algorithms (e.g., artificial neural networks, Bayesian statistics, support vector machines, decision trees, classifiers, k-nearest neighbor, etc.), unsupervised learning algorithms (e.g., artificial neural networks, association rule learning, hierarchical clustering, cluster analysis, etc.), semi-supervised learning algorithms, deep learning algorithms, etc. In at least one example, the example inputs can include previously received specified data 114, previously stored rule(s), rule(s) generated responsive to receiving particular specified data 114, data output from the validation module 124, etc.

Block 408 illustrates adding the one or more rules to a database storing the existing rule(s). Based at least in part on generating one or more rules, the rule generation module 128 can store the new rule(s) in the rule database 136.

As described above, the rule database 136 can store rule(s) that are particular to a type of incoming data to be analyzed and validated based on techniques described herein. For instance, techniques described herein can be used to validate subscriber and partner utilization and engagement data, plan accounting reconciliation reports, claims data, provider data, etc. In such examples, the rule database 136 can store different rule(s) that can be dynamically determined for the particular data sets.

FIG. 5 illustrates an example process 500 for determining a threshold for validating a data file. As described above, thresholds can be dynamically changed depending on variables associated with the submission of a data file, such as attribute(s) associated with the sponsor (e.g., geographic location, business domain, business size, attrition rate, etc.), attribute(s) associated with a sponsor service provider, attribute(s) associated with a partner, attribute(s) associated with a record and/or set of record(s), a time of day, a time of month, a time of year, a season, etc. That is, techniques described herein can be intelligent in that the thresholds can change without human interaction to change the thresholds. As described below with respect to FIG. 5, the thresholds can be determined using data models and/or machine learning mechanisms.

Block 502 illustrates determining, for a data file associated with a sponsor, at least one of attribute(s) associated with the sponsor, attribute(s) associated with a sponsor service provider, attribute(s) associated with a partner, attribute(s) associated with a record and/or set of record(s), a time of day, a time of month, a time of year, or a season. In at least one example, the threshold determination module 130 can determine at least one of attribute(s) associated with the sponsor, attribute(s) associated with a sponsor service provider, attribute(s) associated with a partner, attribute(s) associated with a record and/or set of record(s), a time of day, a time of month, a time of year, or a season associated with the submission of the data file 110. In some examples, the threshold determination module 130 can utilize metadata associated with the data file 110 to determine such information. In additional and/or alternative examples, the server(s) 104 can store a database with information about sponsor(s) (not pictured in FIG. 1) and, based on receiving a data file from a particular sponsor, the threshold determination module 130 can perform a look-up or other search to obtain data associated with the particular sponsor.

Block 504 illustrates determining, based at least in part on a data model and at least one of attribute(s) associated with the sponsor, attribute(s) associated with a sponsor service provider, attribute(s) associated with a partner, attribute(s) associated with a record and/or set of record(s), the time of day, the time of month, the time of year, or the season, a threshold associated with a rule, the threshold indicating an amount of change to the record database (associated with a characteristic corresponding to the rule) that is permissible for the sponsor and/or the data file. As described above, the threshold determination module 130 can be configured to determine thresholds for rules. That is, in at least one example, the threshold determination module 130 can be configured to determine what percentage (or other metric) of change is permissible given certain variables associated with the data file. As described above, each rule can be associated with one or more thresholds. Each threshold can be associated with a particular sponsor. The certain variables can be based on attribute(s) associated with a sponsor, including, but not limited to, a geolocation of the sponsor, a business domain of the sponsor, a business size of the sponsor, an attrition rate associated with the sponsor, etc., attribute(s) associated with a sponsor service provider, attribute(s) associated with a partner, attribute(s) associated with a record and/or set of record(s), and/or information associated with the submission of the data file, including, but not limited to, a time of day, a time of month, a time of year, a season, etc. In some examples, the threshold determination module 130 can employ one or more data models and/or can apply one or more metrics to determine a threshold for particular rules. Several examples of suitable data models that can be used to predict a threshold can include regression models, such as linear regression models, and stochastic models, such as Markov models, hidden Markov models, and so forth. Additionally and/or alternatively, various reasoning systems can be utilized to determine threshold(s). For instance, the threshold determination module 130 can utilize forward chaining, opportunistic reasoning, or other inference-based methods to determine threshold(s).

In some examples, the threshold determination module 130 can train a data model via machine learning mechanism(s) to determine what percentage (or other metric) of change is permissible given certain variables, as described above. In at least one example, the threshold determination module 130 may utilize a machine learning mechanism to build, modify, or otherwise utilize data model(s) that are created from example inputs and makes predictions or decisions. In such an example, the data model(s) may be trained using supervised learning algorithms (e.g., artificial neural networks, Bayesian statistics, support vector machines, decision trees, classifiers, k-nearest neighbor, etc.), unsupervised learning algorithms (e.g., artificial neural networks, association rule learning, hierarchical clustering, cluster analysis, etc.), semi-supervised learning algorithms, deep learning algorithms, etc. In at least one example, the example inputs can include previously received data files, modification data associated with the data files, attribute(s) associated with particular sponsors, attribute(s) associated with a sponsor service provider, attribute(s) associated with a partner, attribute(s) associated with a record and/or set of record(s) information associated with submission of the data file (e.g., a time of day, a time of month, a time of year, a season, etc.), and indications as to whether the data files were added to the record database 132 (e.g., due to a determination that the particular data file was valid) or not added to the record database 132 (e.g., due to a determination that the particular data file was not valid). Based at least in part on the inputs, the threshold determination module 130 can build, modify, or otherwise utilize data model(s) to make a prediction with respect to an appropriate threshold of change for a particular rule.

For a particular rule, the threshold determination module 130 can employ one or more data models and/or can apply one or more metrics to determine a threshold for the particular rule, and/or the threshold determination module 130 can leverage the data model(s) to predict a threshold for the rule.

Block 506 illustrates comparing the threshold with modification data associated with the data file to determine whether the data file is valid, as described above with reference to FIGS. 2 and 3. In at least one example, the validation module 124 can compare modification data associated with the data file 110 with the threshold, to determine how the change to be implemented by the data file 110 (to the record database 132) relates to the threshold. Based on determining that the change to be implemented by the data file 110 is below the threshold, the validation module 124 can determine that that data file 110 satisfies the rule. The validation module 124 can repeat the same process for each rule, and respective threshold, that is relevant to the data file 110, as described above.

The threshold determination module 130 can update the data model(s) for determining threshold(s) over time. That is, in at least one example, outputs of the validation module 124 can be utilized by the threshold determination module 130 to update the data model(s) over time.

Figure 6:
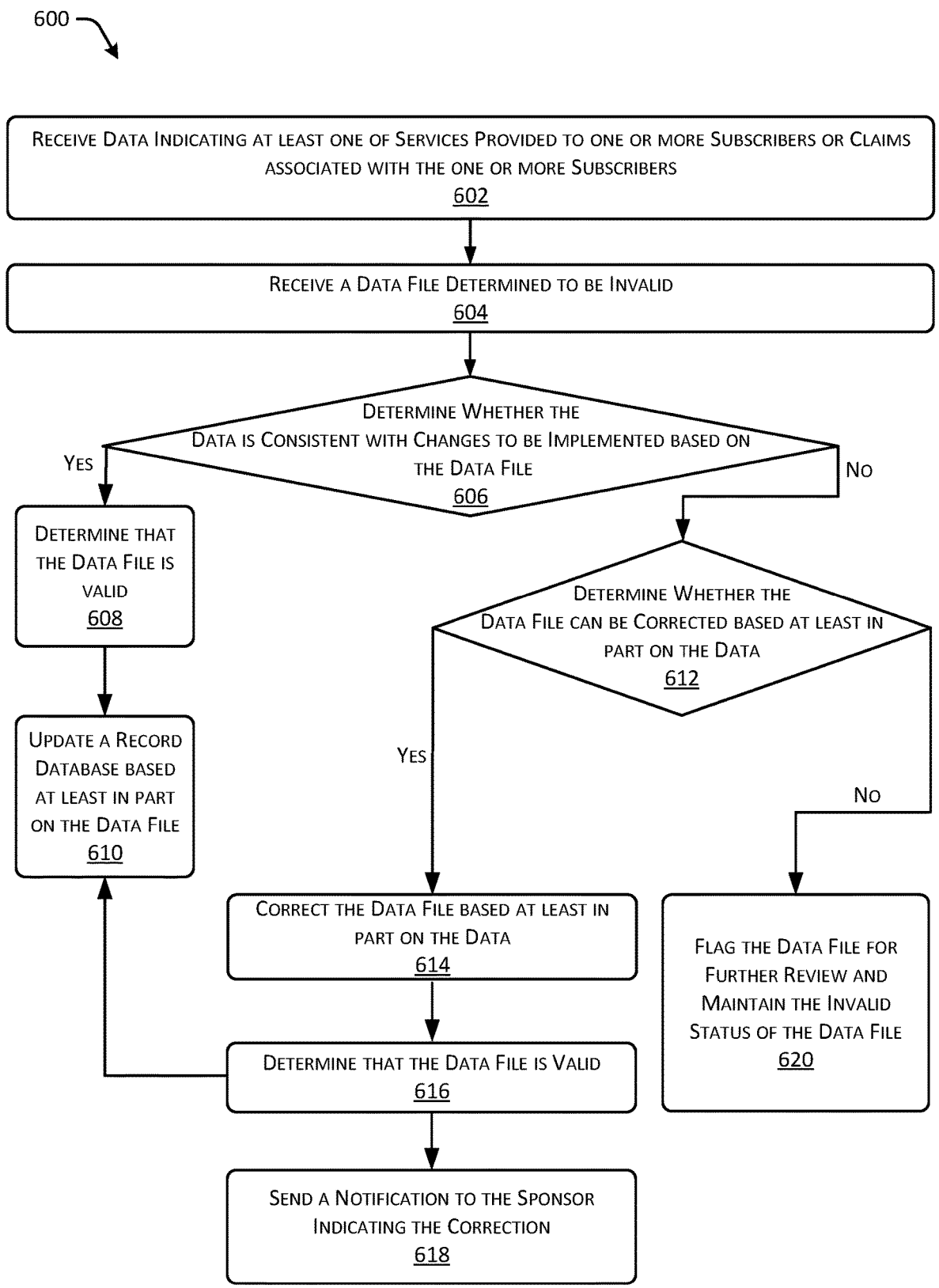
FIG. 6 illustrates an example process for error handling associated with invalid data files.

FIG. 6 illustrates an example process 600 for error handling associated with invalid data files. As described, responsive to determining that a data file 110 is not valid, the validation module 124 can send the data file 110 to the error handling module 126. In some examples, the error handling module 126 can send a notification to the sponsor computing device(s) 102 to notify the sponsors that the data file 110 likely includes an error. In additional and/or alternative examples, the error handling module 126 can send the data file 110 to a queue for manual review by a human analyst.

Furthermore, the error handling module 126 can leverage other data received by the server(s) 104 to evaluate the data file 110, as described below.

Block 602 illustrates receiving data indicating at least one of services provided to one or more subscribers or claims associated with the one or more subscribers. As described above, in some examples, the server(s) 104 can receive data from the partner computing device(s) 108 and/or other sources and/or systems (e.g., healthcare provider computing device(s), etc.). The data can include, but is not limited to, healthcare provider bills, records of services provided to subscribers, claims submissions, etc.

Block 604 illustrates receiving a data file determined to be invalid. Based on determining that change to be implemented by a data file 110 meets or exceeds a particular threshold of a rule, as described above with reference to FIGS. 2 and 3, the validation module 124 can determine that that data file 110 may not be valid and can send the data file 110 to the error handling module 126.

Block 606 illustrates determining whether the data is consistent with changes to be implemented based on the data file. In at least one example, the error handling module 126 can analyze the data received from the partner computing device(s) 108 and/or other sources and/or systems (e.g., healthcare provider computing device(s), etc.) to determine whether the data file 110 does in fact include an error. For instance, the error handling module 126 can compare healthcare provider bills, records of services provided to subscribers, claims submissions, etc. to determine if a change included in the data file 110 is accurate. Based at least in part on determining that the data is consistent with the changes to be implemented based on the data file 110, the error handling module 126 can determine that the data file 110 is valid, as illustrated in block 608.

Block 610 illustrates updating the record database based at least in part on the data file. Based at least in part on determining that the data file 110 is valid, the validation module 124 can send an instruction to the database management module 122 to update the record database 132 based at least in part on the data file 110. Responsive to receiving the instruction to update the record database 132, the database management module 122 can add the data file 110 to the record database 132 and/or update the record database 132 to include information from the data file 110.

Based at least in part on determining that the data is inconsistent with the changes to be implemented based on the data file 110, the error handling module 126 can determine whether the data file can be corrected based at least in part on the data, as illustrated in block 612. That is, in at least one example, the error handling module 126 can evaluate the data to determine whether the amount of data (e.g., the sample size) is above a threshold and/or a confidence level associated with the data is above a threshold such that the error handling module 126 can confidently correct the data file 110.

Based at least in part on determining that the data file can be corrected, the error handling module 126 can correct the data file 110 based on the data, as illustrated in block 614. Accordingly, the error handling module 126 can correct at least part of a dataset associated with the data file 110 based at least in part on the data received from the partner computing device(s) 108 and/or other sources and/or systems (e.g., healthcare provider computing device(s), etc.).

Block 616 illustrates determining that the data file is valid. Based at least in part on correcting the data file 110, the validation module 124 can determine that the data file 110 is valid. Based on determining that the data file 110 is valid, the validation module 124 can send an instruction to the database management module 122 to update the record database 132 based at least in part on the data file 110, as illustrated in block 510.

Block 618 illustrates sending a notification to the sponsor indicating the correction. In at least one example, the error handling module 126 can send a notification to the sponsor computing device(s) 102 to notify the sponsor that the data file 110 was erroneous and that the correction has been made.

Based at least in part on determining that the data file cannot be corrected, the error handling module 126 can flag the data file 110 for further review and main the invalid status of the data file 110, as illustrated in block 620. That is, based at least in part on determining that the data is insufficient such that the error handling module 126 cannot confidently correct the data file 110, the error handling module 126 can flag the data file for further review (e.g., by a human analyst, etc.) and the data file 110 can remain invalid.

Example Clauses

A. A system comprising: one or more processors; and one or more computer-readable media storing instructions executable by the one or more processors, wherein the instructions program the one or more processors to: receive, from a computing device associated with a sponsor, a first data file including a first dataset of characteristics associated with a plurality of subscribers, the sponsor providing a benefit plan for the plurality of subscribers, one or more benefits of the benefit plan being specified by one or more partners; determine first modification data associated with the first data file, the first modification data indicating a first amount of change associated with the first data file, the first amount of change indicating at least one of a number or a percentage of records in the first data file that will modify previously stored data in a first database, the first database storing eligibility data associated with the plurality of subscribers; retrieve a first rule from a second database, the first rule being associated with a characteristic of the characteristics; compare the first modification data with a first threshold associated with the first rule, the first threshold indicating a second amount of change that is determined to be permissible for the first data file; determine that the first modification data indicates that the first amount of change is less than the first threshold; and update the first database based at least in part on the first data file.

B. The system as paragraph A recites, wherein the first database is a source of truth for at least the sponsor and the one or more partners.

C. The system as any of paragraphs A or B recite, wherein the instructions further program the one or more processors to: receive, from the computing device associated with the sponsor, a second data file including a third dataset of characteristics associated with the plurality of subscribers; determine second modification data associated with the second data file, the second modification data indicating a third amount of change indicating at least one of a number or a percentage of records in the second data file that will modify the previously stored data in the first database; retrieve the first rule from the second database; compare the second modification data with the first threshold associated with the first rule; determine that the second modification data indicates that the third amount of change is greater than or equal to the first threshold; and route the second data file to error handling.

D. The system as paragraph C recites, wherein the instructions further program the one or more processors to process the second data file via error handling based at least in part on: receiving, from one or more other computing devices, data indicating at least one of services provided to the plurality of subscribers or paragraphs associated with the plurality of subscribers; comparing the second data file with the data indicating at least one of services provided to the plurality of subscribers or paragraphs associated with the plurality of subscribers; and modifying the second data file based at least in part on the data indicating at least one of services provided to the plurality of subscribers or paragraphs associated with the plurality of subscribers, wherein modifying the second data file causes the second data file to be valid.

E. The system as any of paragraphs A-D recite, wherein the instructions further program the one or more processors to: retrieve a second rule from the second database, the second rule being associated with a different characteristic of the characteristics; compare the first modification data with a second threshold associated with the second rule, the second threshold indicating a third amount of change that is determined to be permissible for the first data file; determine that the first modification data indicates that the first amount of change is less than the second threshold; and update the first database based at least in part on the first amount of change being less than the first threshold and the second threshold.

F. The system as paragraph E recites, wherein the first rule and the second rule are two rules of a plurality of rules relevant to the first data file, and the instructions further program the one or more processors to determine that the first data file satisfies each rule of the plurality of rules prior to updating the first database.

G. The system as any of paragraphs A-F recite, wherein the instructions further program the one or more processors to determine the first threshold based on at least one of a first attribute of the sponsor, a second attribute of a sponsor service provider, a third attribute of the partner, a time of day, a time of month, a time of year, or a season.

H. The system as any of paragraphs A-G, wherein the instructions further program the one or more processors to: train, via a machine learning mechanism, a data model based at least in part on previously received specified data and at least one rule; prior to retrieving the first rule, receive specified data from the one or more partners; determine the first rule based at least in part on the data model and the specified data; add the first rule to the second database; and repeatedly update the second database to include one or more additional rules based at least in part on at least one of receiving updated specified data or data associated with error handling of one or more previously analyzed data files.

I. The system as paragraph H recites, wherein the instructions further program the one or more processors to: train, via a machine learning mechanism, a data model based at least in part on previously determined modification data associated with previously received data files; and determine the first threshold based at least in part on the data model.

J. A computer-implemented method comprising: accessing a data file including subscriber data corresponding to one or more characteristics associated with at least one subscriber; determining modification data associated with the data file, the modification data indicating a first amount of change to result from modifying previously stored data based on the data file; accessing a rule associated with a characteristic of the one or more characteristics; determining, based at least in part on a source of the data file, a threshold associated with the rule, the threshold indicating a second amount of change that is determined to be permissible for the data file; determining that the first amount of change is less than the threshold; and determining whether the data file is valid based at least in part on determining that the first amount of change is less than the threshold.

K. The computer-implemented method as paragraph J recites, wherein the rule is one rule of a plurality of rules, and the computer-implemented method further comprises: determining that the data file satisfies each rule of the plurality of rules; and based at least in part on determining that the data file satisfies each rule of the plurality of rules, updating a database based at least in part on the data file, the database storing eligibility data associated with the at least one subscriber.

L. The computer-implemented method as any of paragraphs J-K recite, wherein the previously stored data comprises at least one of: a previously validated data file; or a database storing eligibility data associated with the at least one subscriber.

M. The computer-implemented method as any of paragraphs J-L recite, further comprising: accessing specified data indicating one or more criteria for receiving one or more benefits; accessing a database storing a plurality of rules; determining that the database does not include the rule; and determining the rule based at least in part on the specified data.

N. The computer-implemented method as any of paragraphs J-M recite, further comprising: accessing specified data from at least one of a partner, an administrator, or other entity; generating, based at least in part on a data model trained via a machine learning mechanism and the specified data, one or more rules; and adding the one or more rules to a database storing a plurality of rules, the one or more rules utilized for analyzing incoming data files.

O. The computer-implemented method as any of paragraphs J-N recite, further comprising determining the threshold utilizing a data model trained via a machine learning mechanism.

P. A computer-implemented method comprising: accessing first data indicating a set of first characteristics having relevance to a first entity; determining at least one rule of a plurality of rules based at least in part on the set of first characteristics; accessing a data file associated with a second entity, the data file including second data corresponding to one or more second characteristics associated with at least one third entity; determining modification data associated with the data file, the modification data indicating an amount of change to result from modifying previously stored data based on the data file; analyzing the modification data based at least in part on a plurality of thresholds associated with the plurality of rules, each rule of the plurality of rules being associated with a threshold of the plurality of thresholds, each threshold indicating a respective amount of change that is determined to be permissible for the data file; and determining whether the data file is valid based at least in part on analyzing the modification data based at least in part on the plurality of thresholds.

Q. The computer-implemented method as paragraph P recites, wherein analyzing the modification data based at least in part on the plurality of rules comprises: accessing the rule; determining, based at least in part on the second entity, a particular threshold associated with the rule; determining that the amount of change is less than the particular threshold; determining that the data file is valid based at least in part on determining that the amount of change is less than the particular threshold; and modifying a database based at least in part on the data file.

R. The computer-implemented method as any of paragraphs P-Q recite, further comprising: accessing the rule; determining, based at least in part on the second entity, a particular threshold associated with the rule; determining that the amount of change is greater than or equal to the particular threshold; determining that the data file is not valid; and routing the data file to error handling for further processing.

S. The computer-implemented method as any of paragraphs P-R recite, further comprising: training, via a machine learning mechanism and based at least in part on previously determined modification data associated with previously received data files, a data model; and determining at least one threshold of the plurality of thresholds utilizing the data model.

T. The computer-implemented method as any of paragraphs P-S recite, further comprising: determining that a database storing at least a portion of the plurality of rules does not include a particular rule for a characteristic of the set of first characteristics; and determining the at least one rule based at least in part on analyzing the first data indicating the set of first characteristics with a data model trained via a machine learning mechanism.

While paragraphs A-I are described above with respect to a system, it is understood in the context of this document that the content of paragraphs A-I may also be implemented via a method, device, and/or computer storage media. While paragraphs I-T are described above with respect to a method, it is understood in the context of this document that the content of paragraphs I-T may also be implemented via a system, device, and/or computer storage media.

Although the subject matter has been described in language specific to structural data items and/or methodological acts, it is to be understood that the subject matter defined in the appended claims is not necessarily limited to the specific data items or acts described. Rather, the specific data items and acts are disclosed as exemplary forms of implementing the claims.

What is claimed is:

1. A computer-implemented method comprising:
    accessing a data file including subscriber data corresponding to one or more characteristics associated with at least one subscriber;
    determining modification data associated with the data file, the modification data indicating a first amount of change to result from modifying previously stored data in a database based on the data file;
    accessing a rule associated with a characteristic of the one or more characteristics;
    determining, based at least in part on a source of the data file, a threshold associated with the rule, the threshold indicating a second amount of change that is determined to be permissible for the data file;
    determining that the first amount of change is less than the threshold;
    determining that the data file is valid based at least in part on determining that the first amount of change is less than the threshold; and
    updating, in response to determining that the data file is valid, the database based at least in part on the data file.

2. The computer-implemented method as claim 1 recites, wherein:
    the rule is one rule of a plurality of rules,
    the database is updated in response to determining that the data file satisfies each rule of the plurality of rules, and
    the database stores eligibility data associated with the at least one subscriber.

3. The computer-implemented method as claim 1 recites, wherein the previously stored data comprises at least one of:
a previously validated data file, or
eligibility data associated with the at least one subscriber.

4. The computer-implemented method as claim 1 recites, further comprising:
accessing specified data indicating one or more criteria for receiving one or more benefits; and
generating the rule based at least in part on the specified data.

5. The computer-implemented method as claim 1 recites, further comprising:
accessing specified data from at least one of a partner, an administrator, or other entity;
generating, based at least in part on a data model trained via a machine learning mechanism and the specified data, one or more rules; and
adding the one or more rules to a rule database storing a plurality of rules, the one or more rules utilized for analyzing incoming data files.

6. The computer-implemented method as claim 1 recites, further comprising determining the threshold utilizing a data model trained via a machine learning mechanism.

7. The computer-implemented method as claim 1 recites, wherein the rule is a first rule of a plurality of rules, the plurality of rules is associated with a plurality of weights, and the computer-implemented method further comprises:
determining a second threshold associated with a second rule of the plurality of rules;
determining that the first amount of change is above the second threshold; and
determining that a weight, of the plurality of weights, associated with the second rule indicates that the second rule does not preclude updating the database based at least in part on the data file.

8. The computer-implemented method as claim 1 recites, further comprising:
accessing a second data file including second subscriber data corresponding to one or more second characteristics associated with the at least one subscriber;
determining second modification data associated with the second data file, the second modification data indicating a third amount of change to result from modifying the previously stored data in the database based on the second data file;
accessing a second rule associated with a second characteristic of the one or more second characteristics;
determining a second threshold associated with the second rule;
determining that the third amount of change is above the second threshold; and
routing the second data file to an error handling module, based on determining that the third amount of change is above the second threshold.

9. The computer-implemented method as claim 8 recites, further comprising adjusting, via a machine learning mechanism, the second rule based on a response from the error handling module.

10. A computer-implemented method comprising:
accessing first data indicating a set of first characteristics having relevance to a first entity;
determining at least one rule of a plurality of rules based at least in part on the set of first characteristics;
accessing a data file associated with a second entity, the data file including second data corresponding to one or more second characteristics associated with at least one third entity;
determining modification data associated with the data file, the modification data indicating an amount of change to result from modifying previously stored data in a database based on the data file;
analyzing the modification data based at least in part on a plurality of thresholds associated with the plurality of rules, each rule of the plurality of rules being associated with a threshold of the plurality of thresholds, and each threshold indicating a respective amount of change that is determined to be permissible for the data file;
determining that the data file is valid based at least in part on determining that the amount of change is less than individual thresholds of the plurality of thresholds; and
updating, in response to determining that the data file is valid, the database based at least in part on the data file.

11. The computer-implemented method as claim 10 recites, wherein:
analyzing the modification data based at least in part on the plurality of rules comprises:
accessing a rule of the plurality of rules;
determining, based at least in part on the second entity, a particular threshold associated with the rule; and
determining that the amount of change is less than the particular threshold, and
determining that the data file is valid is based at least in part on determining that the amount of change is less than the particular threshold.

12. The computer-implemented method as claim 10 recites, further comprising:
accessing a second data file including third data corresponding to one or more third characteristics associated with a fourth entity;
determining second modification data associated with the second data file, the second modification data indicating a second amount of change to result from modifying the previously stored data in the database based on the second data file;
analyzing the second modification data based at least in part on the plurality of thresholds;
determining that the second amount of change is greater than or equal to a threshold associated with at least one rule of the plurality of rules;
determining that the second data file is not valid based on determining that the second amount of change is greater than or equal to the threshold; and
routing, in response to determining that the second data file is not valid, the second data file to an error handling an system for further processing.

13. The computer-implemented method as claim 10 recites, further comprising:
training, via a machine learning mechanism and based at least in part on previously determined modification data associated with previously received data files, a data model; and
determining at least one threshold of the plurality of thresholds utilizing the data model.

14. The computer-implemented method as claim 10 recites, further comprising:
generating the at least one rule based at least in part on analyzing the first data indicating the set of first characteristics with a data model trained via a machine learning mechanism.

15. A system comprising:
one or more processors; and
one or more computer-readable media storing instructions executable by the one or more processors, wherein the instructions program the one or more processors to:

access a data file including subscriber data corresponding to one or more characteristics associated with at least one subscriber;

determine modification data associated with the data file, the modification data indicating a first amount of change to result from modifying previously stored data in a database based on the data file;

access a rule associated with a characteristic of the one or more characteristics;

determine, based at least in part on a source of the data file, a threshold associated with the rule, the threshold indicating a second amount of change that is determined to be permissible for the data file;

determine that the first amount of change is less than the threshold;

determine that the data file is valid based at least in part on determining that the first amount of change is less than the threshold; and update, in response to determining that the data file is valid, the database based at least in part on the data file.

16. The system as claim 15 recites, wherein:

the rule is one rule of a plurality of rules, the database is updated in response to determining that the data file satisfies each rule of the plurality of rules, and the database stores eligibility data associated with the at least one subscriber.

17. The system as claim 15 recites, wherein the previously stored data comprises at least one of:

a previously validated data file, or eligibility data associated with the at least one subscriber.

18. The system as claim 15 recites, wherein the instructions further program the one or more processors to:

access specified data indicating one or more criteria for receiving one or more benefits; and generate the rule based at least in part on the specified data.

19. The system as claim 15 recites, wherein the instructions further program the one or more processors to:

access specified data from at least one of a partner, an administrator, or other entity;

generate, based at least in part on a data model trained via a machine learning mechanism and the specified data, one or more rules; and add the one or more rules to a rule database storing a plurality of rules, the one or more rules utilized for analyzing incoming data files.

20. The system as claim 15 recites, wherein the instructions further program the one or more processors to determine the threshold utilizing a data model trained via a machine learning mechanism.

* * * * *